United States Patent
Bettle, III

(10) Patent No.: US 8,101,163 B2
(45) Date of Patent: Jan. 24, 2012

(54) TRANSDERMAL COMPOSITIONS

(75) Inventor: Griscom Bettle, III, Sarasota, FL (US)

(73) Assignee: Microdermis Corporation, Princeton, NJ (US)

( * ) Notice: Subject to any disclaimer, the term of this patent is extended or adjusted under 35 U.S.C. 154(b) by 0 days.

(21) Appl. No.: 12/630,690

(22) Filed: Dec. 3, 2009

(65) Prior Publication Data

US 2010/0203005 A1    Aug. 12, 2010

Related U.S. Application Data

(62) Division of application No. 10/670,034, filed on Sep. 22, 2003, now abandoned.

(60) Provisional application No. 60/412,437, filed on Sep. 20, 2002.

(51) Int. Cl.
*A61K 31/74* (2006.01)

(52) U.S. Cl. ............ 424/78.07; 514/788; 514/786; 514/552; 514/549; 424/726; 424/523; 424/744; 554/224; 554/227

(58) Field of Classification Search .............. None
See application file for complete search history.

(56) References Cited

U.S. PATENT DOCUMENTS

| | | | |
|---|---|---|---|
| 2,739,922 A | 3/1956 | Shelanski | |
| 3,941,783 A | 3/1976 | Grega et al. | |
| 3,995,059 A | 11/1976 | Fukumaru et al. | |
| 4,797,408 A | 1/1989 | McGovern et al. | |
| 4,877,789 A | 10/1989 | Shroot et al. | |
| 5,455,273 A | 10/1995 | Maier et al. | |
| 6,645,507 B2 | 11/2003 | Bettle et al. | |
| 6,645,510 B1 | 11/2003 | Coury et al. | |
| 2003/0044435 A1 | 3/2003 | Bettle et al. | |
| 2003/0104018 A1 | 6/2003 | Bettle et al. | |

FOREIGN PATENT DOCUMENTS

| | | |
|---|---|---|
| GB | 1110612 | 4/1968 |
| JP | 1989-201352 | 8/1989 |
| JP | 05-163203 | 6/1993 |

OTHER PUBLICATIONS

Chem. Abstr. JP 59-127068, 1984.*
Prestwich et al., "Syn. of Fluorolipids: 1-O-Alkyl-2,3-O-diacylglycerols as Target Insecticides" J. Agric. Food Chem. vol. 29, pp. 1018-1022, 1981.*
Chem. Abstr., Oswald et al., The synthesis of 14C- and 3H- labeled glycerol ethers, Lipids, pp. 241-246, 1966.*
Weber et al., European Journal of Biochem., vol. 146, No. 2, pp. 323-329, 1985 and Chem Abstr. 102:146207, 1985.*
Abstract of JP-05/163203, 1993.
Abstract of JP-01/201352, 1989.
Chang et al., JACS, 124(9), pp. 1856-1857, 2020, web release Feb. 2002.
Chem abstrs. of US4797408, US5455273, US3941783, US3995059.

* cited by examiner

*Primary Examiner* — Deborah D Carr
(74) *Attorney, Agent, or Firm* — Choate Hall & Stewart LLP; Brenda Herschbach Jarrell

(57) ABSTRACT

The present invention is directed to transdermal compositions and the uses thereof. These compositions include at least one of the following components: a $C_1$-$C_6$ dialkyl, $C_{12}$-$C_{30}$ dialkyl quaternary ammonium salt, a $C_{12}$-$C_{30}$ fatty acid, a nitrogenous organic base, $C_{12-30}$ fatty alcohol, monoglyceride or the reaction products thereof.

41 Claims, 5 Drawing Sheets

TRANSDERMAL COMPOSITIONS

RELATED APPLICATION

The present application is a divisional application of application U.S. Ser. No. 10/670,034, filed on Sep. 22, 2003 now abandoned, which claims priority of provisional application U.S. Ser. No. 60/412,437, filed on Sep. 20, 2002.

BACKGROUND OF THE DISCLOSURE

1. Field of the Invention

The present invention is directed to compositions useful as a carrier for transdermal compositions. These compositions are also useful, in combination with active agents, in the treatment of skin diseases, skin injuries, chronic skin conditions and the like. The transdermal compositions of the present invention are directed to products formed by the reaction of combinations of a quaternary ammonium salt, a fatty acid, a fatty alcohol, a nitrogenous base and a monoglyceride.

2. Background of the Prior Art

The design of a composition which, when applied in combination with an active agent, to treat various skin diseases, skin injuries, chronic skin conditions and the like is complex due to the necessity of insuring delivery of the active agent to the proper place on or below skin, providing proper permeation into the skin and providing the desired physical separation, if any, of the composition from the skin surface. A desirable transdermal composition topically delivers medicinal active agent or agents to the dermally affected portions of the body; provides necessary nutrients and building block precursors; promotes normal and/or healing microbial activity at the site of the skin to be treated yet inhibits outside infections caused by external pathogenic bacterial or viruses; and, optimally, modifies electrical charged density in and around the portion of the skin to be treated so as to attract biologically provided nutrients and building block precursors to the site which may have a deficient blood supply.

The above remarks establish the difficulty of designing compositions for transdermal use which meet all of the above requirements of an efficient transdermal composition. However, the problem is multiplied when it is appreciated that the cost of preparing a wide range of effective compositions which meet all of these requirements for all skin conditions is quite imposing. That is, the requirement to meet all of the aforementioned requirements is a function of the skin condition to be treated or the skin malady to be prevented. The requirements of meeting all of the aforementioned conditions depend on the specific condition to be treated or prevented. Thus, a composition which meets all of the requirements mentioned above in the case of a burnt skin may not be effective to meet all of the requirements when a skin irritation is to be treated. In those cases totally different compositions may be utilized. Thus, the costs of providing a wide range of compositions suitable for transdermal compositions is imposing.

The above remarks establish the need in the art for efficient transdermal compositions that may be utilized to prepare a composition for transdermal utilization which can be adjusted by minor additions or subtractions to provide a "universal transdermal composition." It is thus apparent that there is a strong need in the art for a new class of compositions useful for transdermal application which meets all of the requirements for skin treatment and malady prevention without undue expense due to the requirement for a whole plurality of different components.

BRIEF DESCRIPTION OF THE INVENTION

It has now been discovered that new classes of compositions, useful for transdermal applications can be prepared from just a few different compounds if thermodynamic conditions are within certain parameters.

In accordance with the present invention transdermal compositions are provided. These compositions include at least one or more of the following components: a $C_1$-$C_4$ dialkyl, $C_{12}$-$C_{21}$ dialkyl quaternary ammonium salt, a $C_{12}$ to $C_{26}$ fatty acid, a nitrogenous organic base, a $C_{12}$ to $C_{26}$ fatty alcohol and a glycerol ester of a $C_{12}$ to $C_{26}$ fatty acid and the reaction products thereof.

In further accordance with the present invention new compounds formed by reaction of the $C_{12}$-$C_{26}$ fatty acid and the quaternary ammonium salt and the reaction product of the fatty alcohol and the glycerol ester have been discovered.

In another embodiment, the present invention is further directed to new tertiary amides of the formula

or pharmaceutically acceptable salts thereof wherein
$R_4$ is a fatty group having 11-29 carbon atoms.
$R_5$ and $R_6$ are independently lower alkyl, aryl lower alkyl or fatty group of 11-29 carbon atoms or $R_7$;
$R_7$ is $R_1$—Ar—O—$R_2$—O—$R_3$—;
$R_1$ is alkyl group containing 1-15 carbon atoms;
$R_2$ and $R_3$ are independently lower alkylene groups containing 1-6 carbon atoms and Ar is aryl.

BRIEF DESCRIPTION OF THE DRAWINGS

The present invention may be better understood by reference to the accompanying drawings of which.

DETAILED DESCRIPTION

Figure 1:
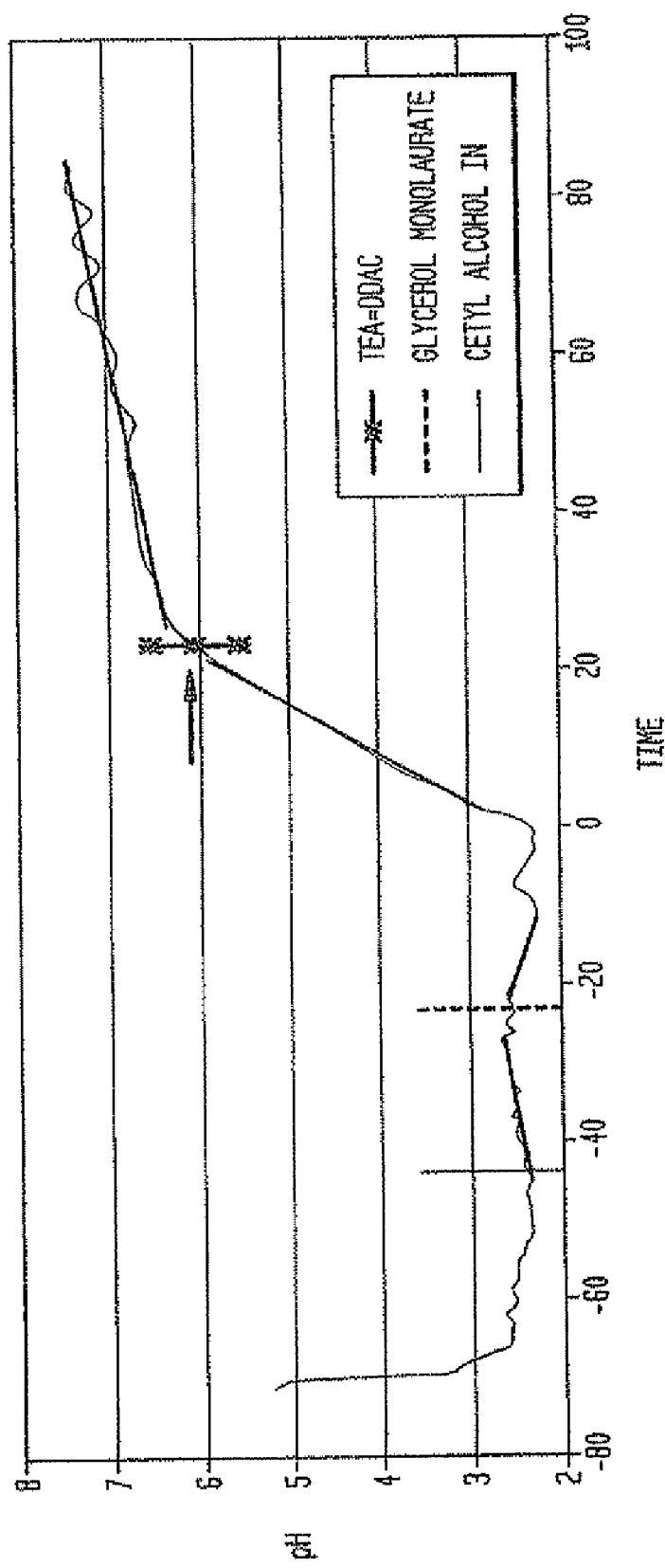
FIG. 1 is a plot of pH as a function of the time before addition of, and the mass of, triethanolamine added in the reaction mixture in Example 10. In the figure, the negative numbers are minutes from TEA addition, while positive numbers are minutes from TEA addition. The - represents cetyl alcohol, --- represents glycerol monolaurate and - represents TEA and DDAC, which are the same amount.

The term "lower alkyl", when used alone or in combination, means an alkyl group containing 1-6 carbon atoms. The lower alkyl group may be branched or straight chained. Preferred lower alkyl contains 1-4 carbon atoms and more preferably 1 or 2 carbon atoms and most preferably methyl. Examples of lower alkyl include methyl, ethyl, propyl, isopropyl, butyl, t-butyl, isobutyl, sec-butyl, pentyl and hexyl.

As used herein, aryl, when used alone or in combination, is an aromatic group comprised solely of carbon ring atoms. The aryl group may be monocyclic, bicyclic or tricyclic. If more than 1 ring is present, the rings are fused; thus the aryl group also includes polynuclear aromatics, i.e., bicyclic and tricyclic fused aromatic rings. The aryl group contains 4n+2 ring carbon atoms, wherein n is 1-4. The aryl group contains 6, 10, 14 or 18 ring carbon atoms and up to a total of 25 carbon atoms. It is preferred that n is 1-3. The preferred aryl groups are phenyl, naphthalene, including alpha and Beta-naphthalene, anthracene, phenanthrene, and the like. The most preferred aryl group is naphthalene, but especially phenyl.

The aryl group may be unsubstituted or substituted with one or more electron donating groups or electron withdrawing groups. The terms "electron withdrawing groups" and "electron donating groups" refer to the ability of a substituent to withdraw or donate electrons relative to that of hydrogen if the hydrogen atom occupied the same position in the molecule. These terms are well understood by one skilled in the art and are discussed in Advanced Organic Chemistry, by J. March, 4$^{th}$ Ed. John Wiley and Sons, New York, N.Y. pp. 16-18 (1992), and the discussion therein is incorporated by reference. Examples of electron withdrawing groups include halo, especially fluoro, bromo, chloro, iodo, and the like; nitro; carboxy; formyl; lower alkanoyl; carboxyamido; triloweralkylamino; aryl; trifluoromethyl; aryl lower alkanoyl; lower carbalkoxy; and the like. Examples of electron donating groups include such groups as hydroxy; lower alkoxy, including methoxy, ethoxy, and the like; lower alkyl; amino; lower alkylamino; dilowerlakylamino; aryloxy (such as phenoxy); mercapto; mercapto lower alkyl; lower alkylthio; and the like. One skilled in the art will appreciate that the aforesaid substituents may have electron donating properties under one set of circumstances and electron withdrawing properties under different chemical conditions or circumstances; these are also contemplated to be within the scope of these terms. Moreover, the present invention contemplates any combination of substituents selected from the above-identified terms.

It is preferred that the aryl group is unsubstituted or substituted by lower alkyl groups.

The term "aryl lower alkyl group" refers to a lower alkyl group as defined herein bridging an aryl group, as defined herein, to the main chain. Examples include benzyl, phenethyl, phenpropyl, phenisopropyl, phenbutyl, diphenyl methyl, 1,1-diphenylethyl, 1,2-diphenylethyl, and the like.

The fatty acid or fatty alcohol as used herein may be saturated or unsaturated aliphatic which may be straight or branched chain. It is preferred that the fatty acid contains 12-30 carbon atoms and more preferably 16-22 carbon atoms and most preferably 16-20 carbon atoms. It is also preferred that the aliphatic portion of the fatty acid or fatty alcohol radical is saturated or contains 1-8 carbon-carbon double bonds and more preferably 1-6 carbon-carbon double bonds. In one embodiment, the aliphatic portion of the fatty acid or fatty alcohol contains 1, 2 or 3 carbon-carbon double bonds. Examples include lauric acid, myristic acid, palmitic acid, stearic acid, behenic acid, arachidic acid, oleic acid, linoleic acid, palmitoleic acid, linolenic acid, arachidonic acid and the like.

As used herein, the term "fatty group", when used alone or in combination is a fatty acid group without the terminal carboxy moiety on the omega carbon of the chain.

In other words, it is $R_8$ wherein

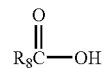

is the corresponding acid. The fatty group ($R_8$) contains 11-29 carbon atoms and more preferably contains an odd number of carbon atoms. Preferably, it contains 15-21 carbon atoms. It may be completely saturated or contain 1-8 carbon-carbon double bonds. It is preferred that the fatty group is saturated or contains one to six carbon-carbon double bonds. However, the fatty group may contain less than six carbon-carbon double bonds, e.g., one or two or three carbon-carbon double bonds. It may be straight chained or branched.

The quaternary ammonium salts used in the present invention include four groups around the central nitrogen atom. They may include combinations of short chain alkyl groups, containing 1-4 carbon atoms, fatty groups, aryl, and aryl lower alkyl group.

In addition, the nitrogen atom in the quaternary ammonium salts or in the tertiary amide may be substituted by $R_7$ wherein $R_7$ is

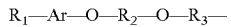

wherein $R_2$ and $R_3$ are lower alkylene groups containing 1-6 carbon atoms, $R_1$ is a lower alkyl group and Ar is aryl. It is preferred that $R_2$ and $R_3$ contains 1-3 carbon atoms and more preferably 1 or 2 carbon atom. It is also preferred that $R_2$ and $R_3$ are the same. It is even more preferred that $R_2$ and $R_3$ are the same and contain 1 or 2 carbon atoms and most especially 2 carbon atoms.

$R_1$ is preferably an alkyl group containing 1-15 carbon atoms and more preferably 1-10 carbon atoms. It may be straight chained or branched.

In the quaternary ammonium salts it is preferred that the central nitrogen atoms is substituted by at least two lower alkyl groups, especially alkyl containing 1-3 carbon atoms and most preferably methyl. It is also preferred that the other two substituents are either aryl, e.g., phenyl, aryl lower alkyl, e.g., benzyl, fatty group or $R_7$.

The quaternary ammonium salts in one embodiment of the present invention contains two lower alkyl groups and two fatty groups. In another embodiment it contains two lower alkyl group and two aryl groups or two aryl lower alkyl groups. In still another embodiment, the quaternary ammonium salt contains two lower alkyl group, one aryl or aryl lower alkyl group and one $R_7$.

It is most preferred that the quaternary ammonium salts contain two lower alkyl groups and two fatty groups or two lower alkyl and, one aryl lower alkyl group and one $R_7$ group, as defined above. The preferred $R_7$ group is

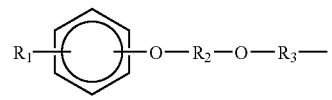

wherein $R_1$, Ar, $R_2$ and $R_3$ are as defined hereinabove.

In a preferred embodiment, the quaternary ammonium salt has the formula

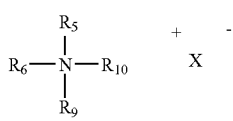

wherein $R_5$ and $R_6$ are as defined hereinabove, $R_9$ and Rio are lower alkyl and X is a counterion.

In a preferred embodiment, the values of $R_5$ and $R_6$ are also as described hereinabove. However it is preferred that $R_5$ and $R_6$ are both independently fatty groups or one of $R_5$ and $R_6$ is an aryl or aryl lower alkyl and the other is $R_7$.

It is preferred that $R_9$ and $R_{10}$ are independently an alkyl group containing 1-3 carbon atoms. It is even more preferred that $R_9$ and $R_{10}$ are the same. It is most preferred that $R_9$ and $R_{10}$ are the same and contain 1-3 carbon atoms. It is especially preferred that $R_9$ and $R_{10}$ are both methyl.

The quaternary ammonium salts consists of a cation portion and a counterion (anion), identified as X. The discussions hereinabove described the cation portion. The counterion is a spectator ion and can be any counterion normally used in the pharmaceutical or cosmetic arts. The preferred counterions (anions) of the quaternary ammonium salts are the halides, especially chlorides. Especially preferred salts within the scope of the quaternary ammonium salts of the present invention include dimethyl distearyl ammonium chloride and dimethyl ditallow ammonium chloride, and dimethyl benzyl benzethonium chloride. Of these, dimethyl distearyl ammonium chloride and dimethyl benzyl benzethonium chloride are most preferred.

It is preferred that the amides of the present invention have the formula

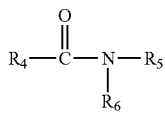

or pharmaceutically acceptable salts thereof wherein $R_5$ and $R_6$ are independently aryl, aryl lower alkyl, fatty group, or $R_7$ and $R_4$ is a fatty group, as defined herein.

The preferred $R_4$ is an aliphatic containing 15-21 carbon atoms. The preferred $R_4$ group is completely saturated or contains 1-8 carbon-carbon double bonds and more preferably 1-6 carbon-carbon double bonds. In one embodiment, the $R_4$ group is saturated or contains 1, 2, 3 or 4 carbon-carbon double bonds. The preferred $R_4$ is as described hereinabove for fatty groups.

The preferred $R_6$ and $R_5$ groups are as described hereinabove.

Examples of preferred tertiary amides of the present invention include benzethonium stearamide, benzethonium linoleamide, distearyl linoleamide and distearyl stearamide.

A first transdermal composition of the present invention includes a quaternary ammonium salt, as defined hereinabove wherein on the cationic portion, two of the substituents on the nitrogen atom are independently an alkyl group having 1-6, and more preferably 1-4 carbon atoms (i.e., a dialkyl group) wherein each alkyl group is the same or different, and the other two groups around the nitrogen atom are independently aryl, aryl lower alkyl, $R_7$, or a $C_{12}$-$C_{30}$ fatty group. The preferred quaternary ammonium salt is as defined hereinabove. The quaternary ammonium salt is particularly suited to the treatment of mammals, e.g., humans, suffering from insect bites. Insect bites cause itching, inflammation and irritation of the skin. Without being bound, it is believed that these conditions are usually caused by injection of formic or similar acids into the skin by the insect. Thus, the ammonium quaternary salts described hereinabove, which are bases having pH's above 7, act to neutralize the acidic affected skin. Moreover, the quaternary ammonium salts in concert with other active agents, such as antioxidants, eliminate the pain and itching associated with insect bites.

The quaternary ammonium salts of the present invention are particularly suited for use in a transdermal composition employed in treating insect bites. Without being bound, it is believed that the long chain radical, non-polar portion of the compound forms a film that surrounds the affected area protecting it from environmental contaminants. At the same time, it is believed that the polar portion of the quaternary ammonium salt aids in neutralizing the acid-induced skin effects of the insect bite. For example, the ammonium salt, such as dimethyl distearyl ammonium chloride acts as a mild base which can neutralize the formic acid in insect bites. Thus, an aspect of the present invention is the use of quaternary ammonium salts as defined herein for the treatment of insect bites in humans. The quaternary ammonium salts are applied topically in effective amounts in a treatment regimen defined by the physician. Preferably, it is applied topically on the skin of the mammal, especially humans, on the locus of the area of the bite in an amount sufficient to be completely rubbed onto the skin, said amount varies depending on several factors, e.g., nature and extent of the affected area, the age of the patient, and the like. Preferably, the amount applied ranges from about 0.3 g to about 1.0 g and more preferably from about 0.5 g to about 0.75 g per 75 kg mammal. The quaternary ammonium salts may be carrier free or may be combined with a pharmaceutical carrier normally used in the pharmaceutical arts to form a pharmaceutical composition, the latter being more preferred.

A second aspect of the present invention is the reaction product ("first product") of the quaternary ammonium salt and a fatty acid as described hereinabove containing 12-30 carbon atoms, or a salt thereof, as defined herein. The preferred fatty acid contains 16-22 carbon atoms. The preferred fatty acid is stearic acid. The reaction is effected under effective conditions. It is preferred that the reaction is conducted in aqueous medium, especially water. It is also preferred that the reaction is conducted with equivalent amounts of the ammonium salt and the fatty acid, although ratios ranging from about 1:10 to about 10:1 may be used. The reaction is effected at temperatures above the melting point of the fatty acid. At the conclusion of the reaction, the pH of the solution decreases very quickly, after formation of the product. For example, when Varisoft, which is dimethyl distearyl ammonium chloride, is reacted with stearic acid at a temperature greater than the melting point of stearic acid, i.e., at a temperature greater than about 50° C., the pH drops exponentially from 5-6 down to 2-3 within minutes of forming the product, dimethyl distearyl ammonium stearate.

The initial reaction product resulting from the reaction of the quaternary ammonium salt and the fatty acid is a quaternary ammonium salt fatty acid complex, hereinafter also referred to as an ion pair.

This reaction product is also useful and can be combined with the quaternary ammonium salt, described hereinabove to form a second transdermal composition.

The second transdermal composition of the present invention is an antiseptic scrub composition employed to remove microorganisms present on objects, such as walls, floors, cabinets, windows, toys, utensils, machinery, doors, toilets, sinks, and the like and to kill microorganisms that are not removed.

The problems associated with antiseptic compositions of the prior art are that they include aggressive detergents and microphobes which are so irritating to the skin that they can make affected portions of the rough skin chapped and/or irritated. The second transdermal composition addresses these problems.

The molar ratio of the quaternary ammonium salt and the reaction product of an ammonium salt and a fatty acid (first product) are such that the molar ratio of ammonium salt to the first product is in the range of between about 10:1 and about 1:10. More preferably, this molar ratio is in the range of between about 5:1 and about 1:5. Still more preferably, this molar ratio is in the range of about 1:2 to about 2:1. Most preferably, the molar ratio is in the range of about 1:1. The second transdermal composition may also contain the antiseptic detergents of the prior art. If present, the antiseptic detergent is present in effective amounts to kill the unwanted microorganisms.

In addition, this second transdermal composition may be carrier free or associated with a carrier normally used in the pharmaceutical or cosmetic arts.

Although the invention is independent of any theory explaining its effectiveness, it is believed, without wishing to be bound, that the ammonium salt provides a protective film to the skin surface while the first reaction product heals the skin of the deleterious effect of the antiseptic active agents. In any event the second transdermal composition, used as an antiseptic agent, for example, as a scrub wash, provides soft, smooth microbiologically benign skin.

A third aspect of the present invention is directed to the reaction product of a quaternary ammonium salt and a fatty acid, or salt thereof, i.e., the ("first product") as defined in the second embodiment, in an aqueous medium, such as water, at a pH less than 4.5 optionally in the presence of a catalytic effective amount of a nitrogenous organic base, for sufficient time for a stable product ("second product") to form. This reaction forms the tertiary amide described hereinabove. The molar ratio of the quaternary ammonium salt and the fatty acid is the same as used in the preparation of the first product. The reaction is effected under conditions sufficient for a product different from the first product to be formed. i.e., for the tertiary amide to be formed. It is preferred that if a base is utilized the base used is an alkanolamine, or alkylamine especially a lower alkanolamine, or lower alkylamine, i.e., an alkanolamine or alkylamine, containing 1-6 carbon atoms in the alkanol or alkyl portion thereof, respectively, and more preferably 2-4 carbon atoms in the alkanol or alkyl portion thereof, respectively. The amine may be substituted with 1, 2 or 3 alkyl groups or alkanol groups or combination thereof. It is especially preferred that the organic base is a triloweralkanolamine, such as e.g., triethanolamine. Examples of the nitrogen containing base include triethanolamine, trimethanolamine, trimethethylamine, triethylamine, tromethamine or a trisaminoalcohol, such as tris(hydroxymethyl)aminomethane or tris (hydroxyethyl methyl)aminoethane. Of these, triethanolamine and tromethamine are the preferred species; the most preferred organic base is triethanolamine. The reaction is effected at a temperature sufficient for a tertiary amide product to form, preferably above the melting point of the fatty acid. Preferably the reaction is effected, above about 60° C. at 1 atm pressure up to the boiling point of the aqueous solvent, i.e., about 100 C. When the quaternary ammonium salt undergoing the reaction contains a methyl group substituent, it is noted that under the reaction conditions, bubbling in the water is observed, indicating that a gas is evolved. For example, if the quaternary ammonium salt has a methyl substitutent thereon, under the reaction conditions, bubbles are observed indicating that a gas is evolved. Without wishing to be bound, it is believed that the gas is methanol. Moreover, if the quaternary ammonium salt undergoing the reaction is originally a salt of dimethyl distearyl ammonium chloride, a product of the reaction is distearyl stearamide, a tertiary amide.

The reaction is effected optionally in the presence of effective amounts of the nitrogenous (nitrogen-containing) organic base to catalyze the formation of the tertiary amide. Preferably, the organic base, if present, is present in a total molar amount ranging from about 0.02 to about 1.0 and more preferably from about 0.30 to about 0.6 and most preferably from about 0.16 to about 0.50 mole thereof per each mole of quaternary ammonium salt. Preferably, the nitrogenous organic base, if utilized, is added into two separate additions, with the molar amount of nitrogenous organic base present in each addition ranging from about 0.01 to about 0.5, more preferably from about 0.15 to about 0.3 and most preferably from about 0.8 to about 0.2 mole per each mole of quaternary ammonium salt.

If, however, the quaternary ammonium salt contains an aryl moiety which may be bonded to the nitrogen atom in the ammonium salt directly or indirectly through an alkylene bridge, e.g., benzyl group or if $R_7$ is present on the nitrogen atom, then a catalyst is optional.

The tertiary amide is formed by reacting the quaternary ammonium salt with a fatty acid $R_8$ COOH in an aqueous solvent under conditions effective as described herein to form the amide. The ammonium salt and the fatty acid are present in effective amounts to form the tertiary amide. Preferably, the molar ratio of ammonium salt to fatty acid ranges from about 10:1 to about 1:10 and more preferably from about 5:1 to about 1:5 and even more preferably from about 2:1 to about 1:1. However, it is most preferable that the molar ratio is about 1:1.

As the neutralized mixture cools, a second acid hydrate forms. This acid hydrate is stable at neutral pH. When the hydrate is forming, it forms an emulsion. Formation of the hydrate is slow and is not complete until the emulsion is at ambient temperature. The pH rises as hydronium ion is removed from solution. Without wishing to be bound, it is believed that the hydrate forms with three tertiary amides.

Figure 4:
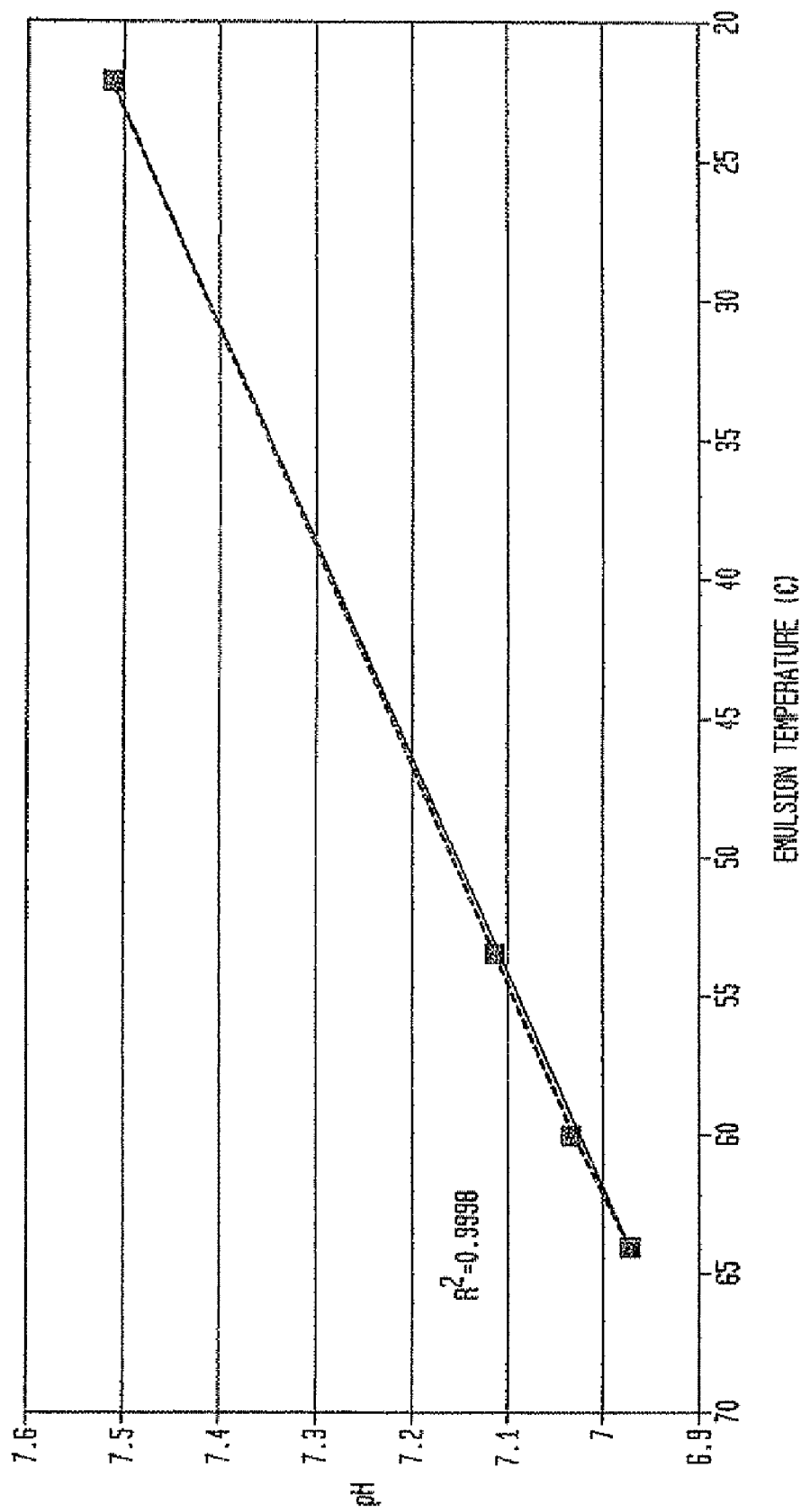
FIG. 4 is a plot of pH as a function of temperature in the formation of the amide hydrate.

FIG. 4 illustrates this rise in pH as the amide hydrate forms. In FIG. 4, Varsoft and benzethonium chloride were reacted with stearic acid to form the tertiary amide. The tertiary amide formed an emulsion. The emulsion is neutralized and made into a finished product. The pH of the product was measured as it cooled to ambient after Carbomer, a polyacrylate thickening agent was added. Carbomer lowers the pH for about 15 minutes as it hydrates (data not shown). The data in FIG. 4 begin after Carbomer hydration is complete and continues until after the product reaches ambient temperature. The pH rises as the emulsion cools. The pH rise is a direct response to the removal of protons from solution as the tertiary amide hydrate is formed. Without wishing to be bound, it is believed that the hydrate has the formula

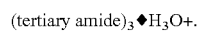
(tertiary amide)$_3$♦H$_3$O+.

Without wishing to be bound it is believed that the quaternary salt and the fatty acid initially produce a quaternary ammonium fatty acid ion pair, in which the ammonium salt and the fatty acid moieties are not covalently bonded, but are held together by electrostatic forces, such as ion dipole interactions, and the like. This ion pair is the first product described hereinabove. It is noted that when the fatty acid and the quaternary ammonium salt react, the pH falls rapidly. Thus hydrogen ions are generated, from the ion pair formulation. The ion pairs can hydrogen bond with the hydrogen ions to form an acid hydrate (protonated ion pair) and remove a proton from solution.

When the protonated ion pair is formed, the pH rises again and the hydronium ion is removed from solution.

If $R_5$ and $R_6$ are a fatty group and the nitrogenous base, as defined hereinabove, is not present, the reaction may just form the ion pair or protonated ion pair, which may be isolated. However, if $R_5$ and $R_6$ are aryl containing groups, such as aryl, arylalkyl and/or $R_7$, then the ion pair may be a fleeting intermediate and the product may proceed to form the tertiary amide.

Without wishing to be bound, it is believed that the protonated ion pair next undergoes a dealkylation reaction, in which $R_9$ and $R_{10}$ react with water to form an alkanol.

For example, in the quaternary ammonium salt, if $R_9$ and $R_{10}$ are methyl, methanol is given off. As indicated hereinabove, a sufficient amount of the catalyst, e.g., weak nitrogenous base, as defined above may be present in amounts sufficient to effect the dealkylation reaction. However, the base is present in sufficient quantities to prevent hard gel formation. It is noted, however, that in some instances, the catalyst may not be needed. For example, when $R_5$ and $R_6$ contain an aryl group, such as aryl alkyl or $R_7$, then a catalyst may not be required to effect the dealkylation. As a result of the dealkylation reaction, a tertiary amide is formed.

Without wishing to be bound, it is believed that the tertiary amide is formed when the two alkyl groups of $R_9$ and $R_{10}$, e.g., such as methyl, of the quaternary ammonium salt, are attacked by a water molecule. The pH falls as the hydronium ion is released; however, as the reaction temperature cools, a tertiary amide hydrate is formed.

Without wishing to be bound, it is believed that the dealkylation occurs by one of the following reaction mechanisms. In one mechanism, the ion pair loses one methyl group by forming methanol with a proton and the carboxylic oxygen atom of the carbon moiety of the fatty acid and becomes an unstable quaternary amide; the methanol is released from the ammonium salt. Then, the second methyl group reacts with water to form the methanol and regenerates a proton and the stable tertiary amide, thereby causing the pH to fall. Alternatively, three ion pairs form an acid hydrate, removing a proton from the aqueous solution, thereby causing the pH to rise. One of the ion pairs reacts with water and the oxygen atom of the carboxy moiety and the fatty acid to form two methanols. The acid hydrate falls apart and releases a proton into the aqueous solution, thereby causing the pH to fall. The remaining unreacted ion pairs form yet another acid hydrate and the pH cycles up and down.

The rate of the reaction to form the tertiary amide is dependent upon the identity of the groups on $R_4$ and $R_5$. For example, where $R_4$ and $R_5$ both contain an aromatic moiety, the amide formation is faster than when $R_4$ and $R_5$ are only fatty groups. Moreover, the amide is formed faster when the fatty acid used as catalyst has a shorter chain. For example, if $R_8$COOH contains 16 carbon atoms, amide formation occurs faster than if it contained 26 carbon atoms. Moreover, if $R_8$ is unsaturated, with one or two double bonds, amide formation is faster than if $R_8$ is completely saturated.

Figure 5:
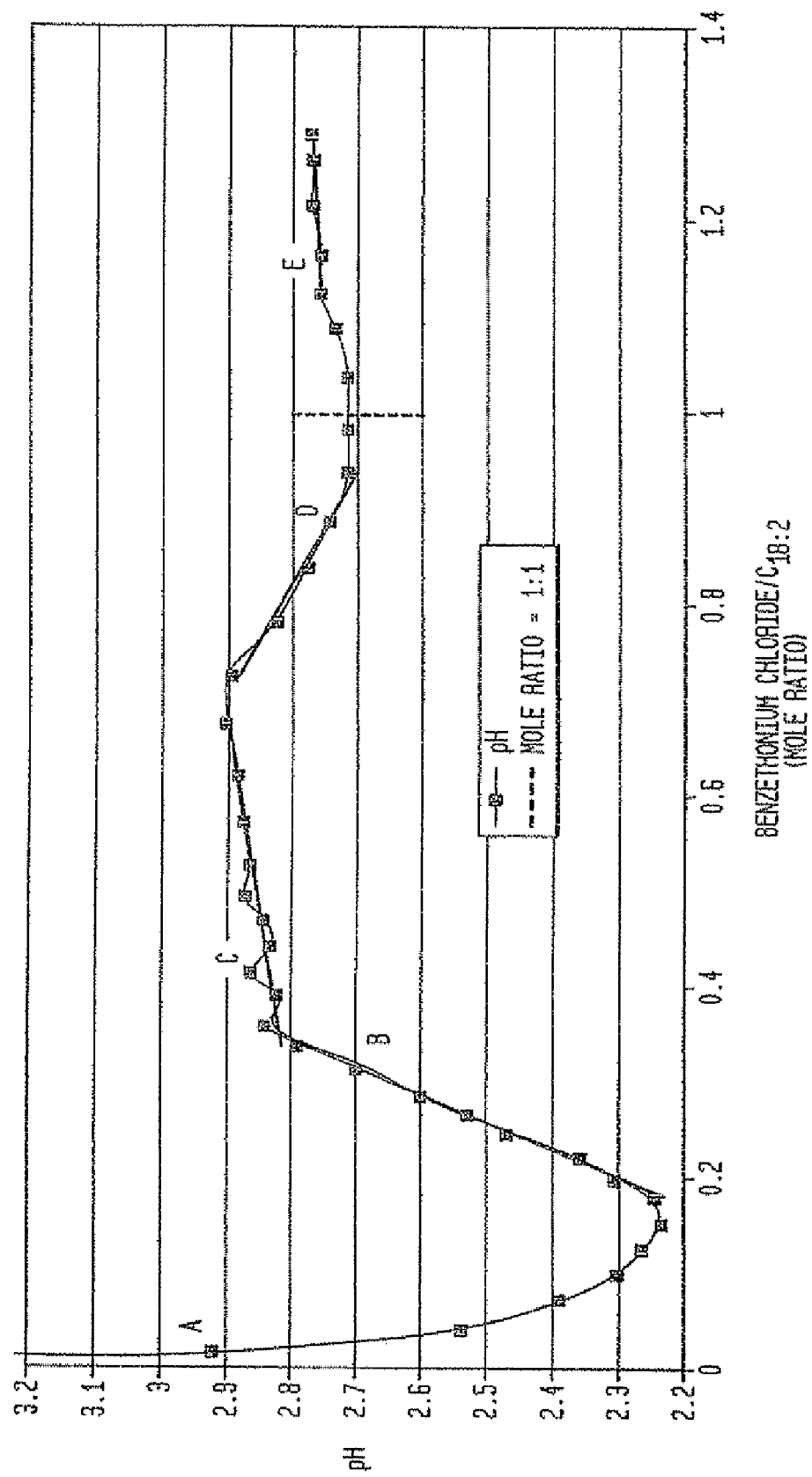
FIG. 5 is a plot versus the mole ratio benzethonium chloride/CLA. In the figure, the ---- represents the line where the mole ratio is 1:1 while - represents the pH. A is stage 1 of the reaction, B is stage 2, C is stage 3, D is stage 4 and E is stage 5.

The various stages are illustrated graphically in FIG. 5. In FIG. 5, benzethonium chloride was titrated into a CLA: water mixture at 70° C. The pH response was monitored as a function of benzenthonium chloride added (unsaturated fatty acid initially in excess). There are five distinct stages clearly shown in the reaction sequences:

1. In stage 1, the pH drops rapidly as the ion pair and proton are formed.
2. In stage 2, the ion pair acid hydrate forms, removing a proton from solution and raising the pH.
3. In stage 3, the ion pair acid hydrate reaction and the tertiary amide formation are occurring simultaneously. One removes a proton the other regenerates a proton. The pH oscillates back and forth at the beginning of this stage then increases slowly.
4. In stage 4, the ion pair acid hydrate converts into the tertiary amide, releases methanol and regenerates a proton.
5. In stage 5, there is no more unreacted fatty acid and the pH stabilizes.

This is the general scheme of the reactions for forming the tertiary amide. After stage 5, however, the pH rises as protons are removed from solution as the positively charged hydrate forms.

The formation of the tertiary amide is inhibited if calcium is present, such as aloe Vera. Aloe Vera contains high levels of calcium. Without wishing to be bound it is believed that calcium can bind with the fatty acids to interrupt the ion pairing mechanism.

Further, if the pH rises above 5, such as by the addition of EDTA or even excess amounts of the nitrogenous containing catalyst described above, then the amide formation is inhibited. These reactions can raise the pH to a level wherein the ion pair hydrate is stable, thus terminating the reaction sequence. Under such conditions, a gel may form.

It is to be also noted that if the quaternary ammonium compound is present in high concentrations, greater than a 10:1 molar ratio relative to the fatty acid, a thick gel is formed. In either case, the gel tends to inhibit the formation of the amide. Without wishing to be bound, it is believed that the gel inhibits the molecular movement needed to orient the ion pair in the acid hydrate. The resulting mixture, the gel, is metastable. If more water is added, the gel dissipates and the amide is generated in situ.

Further, for the reaction to be effected, the temperature of the reaction between the quaternary ammonium salt and the fatty acid is conducted preferably at least above the freezing point of the fatty acid and below the 100° C. boiling point of water, whichever temperature is lower.

It has been found that tertiary amides are effective in penetrating the layers of the skin. Further, the aromatic containing tertiary amides i.e., tertiary amides in which at least one of the substituents on the amide contains an aryl containing group, e.g., aryl, aryl alkyl or $R_7$ are more effective in penetrating the skin than the non-aryl containing tertiary amides i.e., tertiary amides in which all of the groups on the amide are fatty groups. If the fatty group on the tertiary amides, especially the aryl containing tertiary amides is unsaturated, then the tertiary amide penetrates more deeply into the skin as a carrier.

For example, benzethonium stearamide (BSA) penetrates shallowly into the skin and forms a protective fat loving layer on the skin. If it is used in combination with beeswax and povidone, the combination provides a skin protectant that can protect the scalp for thirty minutes from treatment with a highly alkaline hair relaxer.

On the other hand, if the fatty group contains carbon-carbon double bonds, and in addition if the tertiary amide contains aromatic moieties thereon, especially two aromatic moieties, the amide penetrates more deeply into the skin. For example, benzethonium linoleamide (BLA) penetrates deeply into the skin, thereby bringing an active antimicrobial agent into intimate contact with the skin surface. In combination with a nutrient, it enhances the healing rate of burns and cuts. BLA has a strong characteristic smell of unsaturated fatty acid. When rubbed into the skin, there is substantially no characteristic odor on the skin surface and there is a readily perceived greasy coating on the skin. It is believed that the unsaturated fat is within the stratum corneum (SC) and the aromatic substituents on the amide are above and outside the SC.

Moreover, tertiary amides such as BLA, in which the nitrogen amide is substituted with two aryl containing groups and a third group,

wherein $R_8$ is unsaturated are important in sustained pain-free growth of new skin granules.

Without wishing to be bound, it believed that chronic wounds are typically nutrient poor and circulatory poor sites. Excessive stimulation causes pain as blood rushes back into little used capillaries. BLA and other tertiary amides of this class is described in the following paragraph, allows the metering of growth-stimulating nutrients into the chronic wound site.

This effect is more prevalent if a mixture of tertiary amides is applied to the skin, especially two tertiary amides in combination, where they each contain a fatty acid moiety containing 1-8 carbon-carbon bonds as defined herein and more preferably 1-6 carbon-carbon double bonds. It is preferred that at least one of the amide has an aromatic group, i.e., aryl or aryl alkyl or $R_7$ substituted thereon. It is preferred that the two tertiary amides are present in a molar ratio ranging from about 10:1 to about 1:10 and more preferably from about 7.5 to 1 to about 1 to about 7.5 and most preferably from about 3:1 to about 1:3. It is preferred that if one of the tertiary amides have an aromatic substituent thereon, that it is present in the smaller about relative to the tertiary amide having no aromatic moiety thereon, for example, just having fatty groups thereon. Under these circumstances, an enhanced stimulation is effected. For example, if distearyl linoleamide (DSL) is added to BLA in a molar ratio ranging from about 10 to about 1 and more preferably from about 7.5 to about 1 and most preferably from about 3 to about 1, stimulation is more enhanced. However, pain may be felt from this enhanced stimulation. But the pain resulting therefrom can be controlled by adding a topical analgesic such as lidocaine. Nevertheless, healing is fastest when two tertiary amides are used together in effective amounts. In addition, an occlusive moisture barrier, such as beeswax, can be used in chronic wound care products when tertiary amides are used, especially if more than one tertiary amide is utilized, such as BLA and DSL to keep the wound moist. If more than one tertiary amide is utilized, then the tertiary amide is present in effective amounts as above. The beeswax is present in amount sufficient to keep the wound moist, preferably from 0.5 to about 1.5% by weight of the composition. However, where the intact skin is quite thick, such as the skin on the foot, the mixture of aromatic and aliphatic unsaturated tertiary amides, that is, amides in which on one amide, one of $R_4$, $R_5$ and $R_6$ are fatty groups, wherein at least one of the fatty groups is unsaturated and in the other one of $R_4$, $R_5$ and $R_6$ is a fatty group which contains unsaturation and the other two groups contain an aromatic functionality such as $R_7$, aryl lower alkyl, and the like, is quite useful as a carrier. Together, in combination they can penetrate the thick skin as more penetration is required to open the pores sufficient enough to allow nutrients into a thick skin site.

Aliphatic saturated tertiary amides, that is, tertiary amides in which $R_4$, $R_5$ and $R_6$ in the above Formula are only saturated fatty groups, slightly penetrate the skin, allowing moisture to flow out of and functional ingredients, such as nutrients to flow into the stratum corneum (SC). In the absence of an occlusive moisture barrier (eg., beeswax), an aliphatic saturated tertiary amide, e.g., DSS dries out the skin. This property is useful in closing a wound where drying out is important in forming a full durable wound closure. However, with an occlusive barrier, the aliphatic saturated tertiary amides are an effective moisturizer.

The amide hydrates discussed hereinabove are also an effective transdermal carrier; when it is present in effective amounts, they open up the pores and increase the permeability of the skin.

It is to be noted that the amide hydrate forms an emulsion as it cools and may even form a gel, a cracked crust which is unappealing to view. However, applying a shear thereto at a sufficiently high shear rate to cause non-Newtonian flow, air can be whipped therein. As a result, the gel is broken, reformed and the embodiment transformed into a smooth uniform cream.

The tertiary amide or hydrate can also act as a skin protectant when present in skin protecting effective amounts. By skin protectant, it is mean protecting the skin of the mammal from chapping, cracking or contact dermatitis. The preferable amounts are in the ranges indicated hereinabove.

When the tertiary amide hydrate is rubbed onto the skin, it dries completely in about 10 seconds. The dry surface is non sticky and feels like a rubber glove is bonded to the skin. However, it protects the skin from non-ionic surfactants.

Nonionic surfactants, such as Triton X-100 and Nonoxynol-9 and the like are present in many emulsions. These degreasing surfactants are irritating and sticky on the skin.

However, the nonionic detergents can be layered on top of the amide so that they are physically not in contact with skin. As a result, normally irritating ingredients can be added that are not irritating in use. They are present in degreasing effective amounts. More specifically, they are present in amounts ranging from about 1 to about 10% and more preferably from about 2 to about 8% and most preferably from about 4 to about 6% by weight of the composition.

Nutrients and other non-film-forming compounds can be added as another layer on top of the detergent in effective amounts. These nutrients are absorbed into the skin at a rate governed by the concentration of the amide on the skin surface. These nutrients include methyl sulfonyl methane (hereinafter "MSM"), pyrrolidone carboxylic acid (hereinafter "PCA"), Vitamins A, D and K. In addition, they are present in amounts ranging from about 0.5% to about 3% and more preferably from about 1% to about 2% and most preferably from about 1% to about 1.5% of the composition.

A wax layer may be deposited on the nutrient layer, making a uniform, high friction film on the skin surface. The wax film is occlusive and prevents moisture from leaving the skin. The wax layer is present in moisture retarding effective amounts. Preferably, it is present in amounts ranging from about 0.1% to about 2% and more preferably from about 0.5% to about 1.5% and most preferably from about 0.8% to about 1.2% of the transdermal composition. The wax film has an unpleasant hand feel because the coefficient of friction is so high.

Finally, a water-soluble polymer, povidone e.g., polyvinyl pyrolidone (PVP) is added. The polymer is the last layer to deposit and imparts a silky soft hand feel. It is present in amounts ranging from 0.3% to about 3% and more preferably from 0.5% to about 1.5% by weight of the composition.

Without wishing to be bound, it is believed that detergents control the layering of compounds. The tertiary amide acid hydrate has a net positive charge. Intentionally-unreacted cationic surfactants tend to emulsify uncharged waxes, not positively-charged acid hydrates.

The cationic-surfactant-emulsified wax competes with nonionic-emulsified acid hydrate for the negative charge on the skin surface. But the acid hydrate penetrates the SC, giving it a long term advantage over the positively-charged wax. Once the positively-charged acid hydrate is permanently bonded to the SC, the positive charge repels the cationic-wax, creating the first layer.

The nutrient package is nonionic and precipitates after the first layer is formed. As drying continues the intermediate nonionic layer builds up. With increasing distance from the first layer's positive charge, the cationic-wax precipitates and forms a continuous film over the intermediate layer.

The most water soluble film former is povidone. It is the last to dry, so it forms a final film over the first three layers. Povidone has a silky smooth hand feel.

Different products can be made by mixing and matching the layers

For example, a product without the wax and polymer layer allows moisture loss from the skin. This feature is used to let skin surfaces dry out and become durable, tough outer skin.

When rapid absorption of nutrients is desirable, a high concentration of various tertiary amides such as benzethonium linoleamide (BLA), disteraryl linoleamide (DSL), benzethonium stearamide (BSA) and cetyl glycerol laurate (CGL), are used to open the pores for rapid absorption. Preferably these tertiary amides are present in a total amount ranging from about 5% to about 12% and more preferably from about 7% to about 10% and most preferably from about 8% to about 9%. It is preferred that the molar ratio of CGL/DSS/DSL/BLA is about 100/30/20/3. Conversely, when a lower absorption rate of nutrients is desired, for example over 24 hours, only BLA and DSL are used. Preferably they are present in amounts ranging from about 3% to about 4% of the composition. When no absorption is desired, the amide is not present.

The tertiary amides may be prepared by premixing. Premixes are used to simplify processing by executing some of the chemistry separately in a more concentrated formula. By premix, it is meant the composition of the formulation is a mixture of stages 2-5, as described hereinabove in reference to FIG. 5. The premix contains predominantly the tertiary amide in greater than about 50% by weight of the tertiary amide (stage 4) and more preferably greater than 75% by weight of the tertiary amide. It is in gel form that inhibits formation of the amide hydrate (stage 5). However, when placed in water, the premix can spontaneously move through all 5 stages to form the amide hydrate.

The concentration of the premix materially changes the physical chemistry. The aromatic tertiary amide reaction is driven to completion by adding all the fatty acid with the benzethonium chloride (stearic acid:benzethonium chloride mole ratio=2). The aliphatic tertiary amide reaction is incomplete (Varisoft: remaining stearic mole ratio=1) because the viscosity of the mix prevents most of the ion pair acid hydrate from demethylating to the tertiary amide. The combination results in a phase stable grease, rather than a water/solid two phase mixture. The single phase grease is easier to handle than a two phase fluid.

When a premix is added to the main mix and diluted with water such that the tertiary amide can form, the previously incomplete reaction now goes to completion.

Premixes of unsaturated fats are somewhat different than premixes of saturated fats because the unsaturated fats are liquid at room temperature and are harder to make phase stable.

As previously described, the quat/fatty acid conversion to a tertiary amide goes through a meta stable acid hydrate step. Thus, there are believed to be two acid hydrates that can form, one with the ion pair, an intermediate which is meta stable and one with the tertiary amide which is stable and a final product. This step forms a gel at higher concentrations, such as in a premix. If the gel is too thick, then the ion pair acid hydrate formation/demethylation step cannot take place. It is believed that this step forms/deforms and forms again over and over, possibly because only one leg of the ion pair acid hydrate converts to the amide at a time. When this amide is formed, the ion pair acid hydrate breaks up. The two remaining ion pairs find a third ion pair and reform the ion pair acid hydrate. This iterative process goes back and forth until all ion pairs have converted to the tertiary amide. Once cooling begins, the tertiary amide can begin to form the phase stable final acid hydrate.

The ion pair acid hydrate is a visible gel; the amide formation releases visible gas and breaks the gel. The pH rises as the gel forms (pH rises as a proton is removed from solution), then falls as the tertiary amide is formed (pH falls as the proton tied up in the acid hydrate is released back into solution).

If the gel is too strong, this iterative process is interrupted and conversion to the tertiary amide is low. There are many factors that influence the strength of the gel:

Absolute Concentration—If the concentration of the reactants is too high, there is not enough free water to circulate the mix without shear. It would be expected to increase the rate of reaction by increasing the concentration of reagents. This is true only up until that point where gel formation prevents the iterative physical process of forming/deforming/reforming the ion pair acid hydrate. [The absolute concentration is determined experimentally, because the ratio of unsaturated to saturated fatty acids and the different quats all affect the onset of excess gelation.]

Shear Thickening—Most fluids are Newtonian or are shear-thinning. Cationic surfactant systems are known to be shear thickening, that is, the more the fluid is sheared, the thicker the fluid becomes. This is true of the premixes described herein. If there is any shear in the system, a gel forms that inhibits the conversion to the tertiary amide. For example, the mix can be stirred slowly without gel formation. With only mild wiping, for example with a spatula, visible gel forms. When the spatula is removed, the gel breaks and a smooth fluid reemerges.

Gas Release—The aromatic tertiary amides are particularly sudsy. Suds tend to create gels that inhibit the conversion to the tertiary amide. For example, the unsaturated aromatic amides are more sudsy than the saturated aromatic amides. If the unsaturated fatty acid, aromatic and aliphatic quats are mixed together, the gas formed by the faster-reacting aromatic quat inhibits the conversion of the aliphatic quat to the tertiary amide because the released-gas dissipates slowly and a gel is formed. The solution is to complete the reaction of the aromatic quat first, allow time for the gas to dissipate, then begin the reaction of the aliphatic quat.

Process Thinning—Organic bases, especially triethanolamine (TEA) are used as a process aid to prevent permanent gel formation. Low levels of TEA tend to thin the mixture and break the gel. However, TEA also increases the pH. At pH>5, the aromatic quat/fatty acid converts to the tertiary amide readily, but the aliphatic quat does not. The aliphatic reaction rate goes rapidly at pH<4. If the TEA/quat mole ratio is about 0.1, then the gel thinning occurs and the reaction pH is <4.

Premix Manufacturing—The best way to make premix is to react the aromatic quat with excess fatty acid, with the TEA/aromatic quat mole ratio=0.1. Sufficient time is allowed for the gas to be generated and released. The reaction temperature is preferably 80-90° C. and the mix is stirred just enough to insure circulation. When the gas is substantially released, aliphatic quats are added equal to the moles of unreacted fatty acid remaining. Additional TEA is added such that the total TEA added equals 0.1 times the aliphatic quat concentration. The secondary gas release from the aliphatic tertiary amide formation is much slower than the aromatic gas release. A gel forms right after the aliphatic quat is added; the gel breaks and the mix flows at low stirring rates; a slow release of gas occurs until the reaction is substantially complete. When the gas release is substantially complete, the mix can be cooled to a phase-stable grease. The total solids concentration is determined experimentally based on the relative ratios of aromatic/aliphatic and unsaturated/saturated fatty acids. Typical initial solids concentrations range from 30-50%.

The second product and the amide hydrate thereof of the present invention is useful separately or in conjunction in a mixture as a vehicle for transporting molecules to the skin. When used as a carrier, the second product and/or its amide hydrate are present in carrier effective amounts. This second product (amide) and/or its hydrate help carry active agents, such as pharmaceuticals, cosmetics, and the like to the skin or epidermis. Thus, this second product and the hydrate are present in the transdermal composition in amounts effective for the active compound to be transported to the skin. Preferably the second product and/or the hydrate separately or in combination are present as a carrier in at least 0.2% (w/w) of the transdermal compositions and more preferably from about 0.3 to about 10% (w/w) of the transdermal composition and more preferably from about 0.4 to about 7% (w/w) and most preferably from about 2 to about 6% (w/w) of the transdermal composition. It is preferably present in a weight ratio ranging from about 0.1 to about 30 relative to the active agent and more preferably from about 1 to about 24 relative to the active agent and most preferably form about 10 to about 20 relative to the active agent.

It has been found that the ability of the carrier defined hereinabove to penetrate the skin is dependent upon the amounts of the carrier present relative to the active agent. At the higher weight ratios of carrier to active ingredient, such as above about 20, there will be a large transdermal effect, such that the transdermal composition containing carrier will penetrate the skin, on the other hand, at the lower ratio of carrier to active ingredient such as about less than 5, there will be a small transdermal effect, and the transdermal composition containing the carrier will only partially penetrate the skin. At the interim ratio, the transdermal composition containing carrier will penetrate the skin partially, to a greater extent than at the lower ratios but not as much as at the higher ratios.

Thus, by controlling the ratios, one can control the amount of penetration of the transdermal compositions comprising carrier and active ingredient associated therewith into the skin.

A fourth aspect of the present invention is the reaction product of a fatty alcohol containing 12-30 carbon atoms which may be saturated or unsaturated with a fatty acid as defined hereinabove under ester forming effective conditions, which ester is reacted with a monoglyceride to form an ether, the final product being an ether-ester (third product). It is preferred that the fatty alcohol contains 16-22 carbon atoms and is either completely saturated or contains 1-8 carbon-carbon double bonds and more preferably 1-6 carbon-carbon double bonds and most preferably 1-3 carbon-carbon double bonds. More preferably, the fatty alcohol contains between about 12 to about 18 carbon atoms. Still more preferably, the fatty alcohol is cetyl alcohol or myristic alcohol. Most preferably, the fatty alcohol is cetyl alcohol.

The fatty acid ester reacts with a monoglyceride. The monoglyceride is formed from the reaction of glycerol with a fatty acid containing 10-26 carbon atoms under esterification conditions. Preferably the reaction is effected in the presence of an acid. The preferred alcohols contain from 16-22 carbon atoms. Although the ester may be formed at the 1 or 2-position of the glycerol, it is preferred that the ester is formed at the 1-position of the glycerol. The fatty acid esterified to the monoglyceride may be saturated containing no-carbon-carbon double bond or unsaturated containing up to eight carbon-carbon double bonds. The monoglyceride may additionally be substituted. For example, the substituents may be one or more alkyl groups, preferably one or more $C_1$-$C_6$ alkyl. The monoglyceride is additionally preferably saturated. A particularly preferred monoglyceride is glycerol monolaurate.

It is important to appreciate that this third reaction product from the reaction of monoglyceride with the fatty acid ester is conducted in an acid environment. That is, the third reaction product is formed in a reaction mixture where the pH is less than about 4.5. The product of the reaction is an ether-ester. The monoglyceride reacts with the fatty acid ester in an effective amount to form the ether-ester product. Preferably, the fatty acid ester and the monoglyceride are present in about equimolar amounts although the molar ratio may range from about 1:10 to about 10:1. For example, when cetyl alcohol is reacted with stearic acid at a pH less than 4.5, the product formed is cetyl stearate. Moreover, when cetyl stearate is reacted with monoglycerol laurate at pH<4.5, the product is cetyl glycerol laurate (an ether-ester).

The third product is also useful as a vehicle or carrier transporting the active component to or through the epidermis of the mammal, e.g., human. It is present in the transdermal composition in carrier effective amounts to transport the active agent to the area of treatment on the skin or through the skin. Preferably the carrier is present in at least 1% (w/w) of the transdermal composition and more preferably from about 2 to about 10% (w/w) of the transdermal composition and even more preferably from about 3 to about 8% (w/w) of the transdermal composition. It is present in a weight ratio of about 1 to about 120 relative to the active agent and more preferably from about 2 to about 110 relative to the active agent and more preferably from about 20 to about 40 relative to the active agent. This product, however, can either carry the product to the skin or through the dermis. Again, as with the other carrier described herein, the greater the weight ratio of the third product to the active ingredient, the greater is the ability of the transdermal composition containing the same to penetrate the dermis. Thus, in a larger ratio, e.g., greater than about 20, this product will penetrate the epidermis to a larger degree than if the ratio is less than about 5, wherein there will be a slight penetration of the dermis. If the ratio is intermediate therebetween, the transdermal composition will penetrate the dermis to a greater degree than that a composition having lower ratio but less than at that of a composition having a higher ratio.

It is believed that the third product has the formula

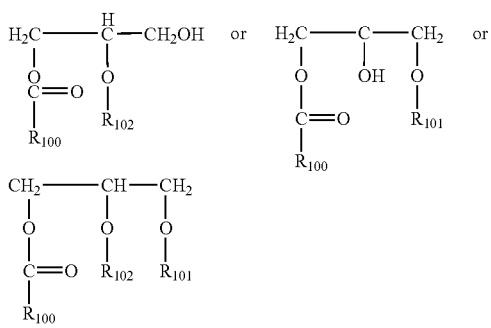

wherein $R_{100}$, is a fatty group, having 11-29 carbon atoms and $R_{101}$ and $R_{102}$ are independently a fatty group containing 12-30 carbon atoms.

It is more preferred that $R_{101}$ and $R_{102}$ contain an even number of carbon atoms. It is even more preferred that $R_{101}$ and $R_{102}$ independently contain 16-22 carbon atoms. Further, it is preferred that $R_{100}$ contains an odd number of carbon atoms. It is even more preferred that 16-22 carbon atoms and $R_{100}$ contain 15-21 carbon atoms. $R_{100}$, $R_{101}$ and $R_{102}$ may contain 0-8 carbon-carbon double bonds and more preferably 0-6 carbon-carbon double bonds. In one embodiment, it may contain 0 carbon-carbon double bonds or 1-3 carbon-carbon double bonds.

A third transdermal composition of the present invention comprises either the amide (the second product defined hereinabove) or the amide hydrate or the third product or both the amide and the third product in association with the quaternary ammonium salt as described hereinabove. The amide (second product) or amide hydrate or the third product or the combination of the third product with the amide (second product) or amide hydrate is present in carrier effective amounts, while the quaternary ammonium salt is present in pharmaceutically effective amounts. Thus, as described herein a pharmaceutical composition comprising the quaternary ammonium salt in effective amounts, as described hereinabove and the second product or the hydrate, or the third product (ether ester), either each alone, or in combination, as the pharmaceutical carrier would be useful for treating bug bites in humans. Moreover, if antioxidants as defined hereinabove are also present, in anti-oxidizing effective amounts, the composition is also useful for alleviating pain and itching associated with insect bites.

Moreover, when the first product described hereinabove, i.e., the reaction product of the nitrogenous ammonium salt with a fatty acid is added to the third product in combination with the detergent as described hereinabove, the composition is useful as an antiseptic scrub composition.

The present invention is directed to other embodiments.

A fourth transdermal composition is useful in healing subcutaneous bruising. The composition contains either the first, second, or third product in carrier effective amounts of the present invention in combination with active agents in therapeutically effective amounts. Such bruising is common in humans of advanced age who are often bruised over much of their bodies, especially their outer extremities. Such bruising is treated by applying this fourth transdermal compositions containing nutrients, such as olive oil, herbs and antioxidants in anti-oxidizing effective amounts. These nutrients are present in amounts effective in eliminating subcutaneous bruising.

Thus, the fourth transdermal composition is a combination of any one of the carriers described hereinabove transporting nutrients through the skin to the site of the bruise. The second product or amide hydrate or third product are present in carrier effective amounts as described hereinabove. Additionally, the application of the fourth transdermal composition to the skin increases blood circulation. This latter property is immediately apparent due to the increased pink color in treated areas of the skin as soon as about 1 to 2 minutes after rub-in of the composition. However, if the desire is to transport the active agent through the dermis, the preferred carrier of the present invention is the third reaction product (ether-ester) which is present in carrier effective amounts as described hereinabove. If the desire is to transport the active agent to the epidermis, the preferred carrier is the second reaction product (amide) or hydrate alone or in combination in effective carrier amounts, as defined herein.

A fifth transdermal composition is useful for treating skin irritations, diaper rash. The skin problems generically referred to as diaper rash extend to humans at the early and late portions of life. That is, infants, as well as the elderly, are subject to the skin problem defined as diaper rash.

Although diapers absorb much of the moisture and bodily discharge, still skin in areas protected by diapers are chronically wet resulting in the formation of rashes and, serious skin infections. This problem is addressed by the fifth transdermal composition.

This transdermal composition includes the quaternary ammonium salt and the second reaction product or amide hydrate alone or in combination. As in the previously described compositions in which the quaternary ammonium salt is a component, the function of the quaternary ammonium salt in this composition is to form a protective film about the skin while the second or fourth reaction product provides the means by which the active agent or agents, the healing compounds, are transdermally conveyed from the skin surface to the damaged layers of the skin. Thus, the two components provide healing and protection. The carrier molecule, second reaction product or hydrate or the third reaction product alone or in combination is present in carrier effective amounts, as defined hereinabove. Moreover, the quaternary ammonium salts are present in pharmaceutically effective amounts, which are the same as defined hereinabove, to form a protective film about the skin. In a preferred fifth transdermal composition, beeswax is additionally present. A particularly effective diaper rash composition includes the fifth transdermal composition and a film forming compound. The film forming compound, preferably beeswax, or beeswax and povidone (polyvinyl pyrolidone), a high molecular weight film forming polymer, is combined with the quaternary ammonium salt in effective amounts to form a protective film on the skin.

The preferred concentration of the amide and the quaternary ammonium salt in this transdermal composition is such that the molar ratio of the total of the second reaction product or hydrate or third reaction product present to the quaternary ammonium salt is in the range of between about 0 to about 5, more preferably from about 0.5 to about 4 and most preferably from about 1 to about 2.

A sixth transdermal composition within the scope of the present invention is employed primarily as a treatment of other skin chafings, e.g., bed sores. Bed sores are the direct result of lingering pressure on the skin of a bed ridden, immobile human beings. This pressure manifests itself in the development of sores which grow progressively more serious as manifested by increasing red color culminating in their more serious manifestation of the breaking open of the skin. Transdermal compositions employed in the treatment of bed sores attempt to treat the skin while, at the same time, strengthen the skin to prevent its rupturing.

The present composition addresses these needs by preventing a bed sore, a reddened area of the skin, from becoming a wound, e.g., rupturing of the skin, by transdermally transporting nutrient active agents deep within the skin. This composition, moreover, acts as a further bed sore preventative by forming a protective film over the area of the skin being treated. As a result, the friction between the skin and bed linens, which precipitate the formation of bed sores, is reduced.

To effectuate these desirable treatment modes, this transdermal composition includes the quaternary ammonium salt in amounts effective to treat the skin chafing, the second reaction product amide or hydrate and the third reaction product (ether-ester) together in carrier effective amounts, as defined hereinabove. The second product or hydrate and the third reaction product transport nutrients deep into the skin cross-section which prevent breakdown of the skin which cause bed sores and increase blood circulation in the affected skin area. The quaternary ammonium compound contributes to the skin treatment by forming a protective film over the treated skin area and is present in amounts sufficient to form a protective film over the treated skin area.

This composition is characterized by concentrations of the three above-described components such that the molar ratio of the quaternary ammonium salt to the second reaction product or amide hydrate to the third reaction product is preferably in the range of about 1:1:1 to about 1:15:20 and more preferably from about 1:2:3 to about 1:10:15 and even more preferably form about 1:3:4 to about 1:6:10. Most preferably this ratio is about 1:4:6.

A seventh transdermal composition is directed to treating skin surface injuries. Skin injuries caused by cuts, skin ulcers and bruising are manifested by primary injury to the skin surface rather than skin deep in the skin. Such injuries are therefore best treated directly at the skin surface. Indeed, components that transmit nutrients to subsurface skin increase blood circulation. Obviously, this is counterproductive in cuts which may open and bleed, in skin ulcers which may cause pain as capillaries suddenly are expanded by increased blood supply and burns in which nutrients are transported past the damaged burn surface site.

To address this unique problem of surface skin damage, this transdermal composition includes the quaternary ammonium salt in therapeutically effective amounts for forming a protective film and the composition comprising the first reaction product and a monoglyceride. The combination of the first reaction product and the monoglyceride tend to heal wounds and do not enhance transmission of nutrients from the skin surface. These properties in combination with the protective film formed by the quaternary ammonium salt effectively retard the flow of nutrients to below the surface site of these types of wounds. Instead, a slow, steady flow of the requisite active agents to the surface site of these wounds is maintained.

The three components of this seventh transdermal composition are preferably present in a molar ratio of quaternary ammonium salt:first reaction product:monoglyceride ranging from about 1:1:2 to about 1:10:15, more preferably from about 1:2:5 to about 1:6:8 and most preferably 1:4:9.

In an eighth embodiment, an active ingredient may be associated with one of the carriers, viz., the ether ester or the amide product. If the active ingredient is to be transported to the skin but not through the skin, it is preferred that the second reaction product is the carrier. On the other hand, if the active ingredient is to transport the active ingredient through the skin, the ether-ester product can be used as the carrier.

Alternatively, the second product or hydrate or the third product, individually or together, may comprise the carrier. They are present in carrier effective amounts.

For example, each may be combined with an antiseptic compound, such as providone-iodine and/or preservative, such as quaternary anti-microbial compounds or triclosan.

These antimicrobial compounds are beneficial on the surface of the skin, but may be detrimental if in the blood stream. Accordingly, a hydrogel for an antimicrobial is formulated comprising the second product (i.e., amide) or hydrate as the carrier.

On the other hand, a topical analgesic compound usually may have an analgesic active ingredient also with a broad range of nutritional ingredients. It is beneficial for the body to absorb this compound over time. In this case, a preferred hydrogel would have both a quaternary ammonium salt, at least one film forming compound and the amide product as the carrier. Such a combination would tend to slow the rate of absorption.

In another embodiment, the transdermal composition comprises as the active ingredient a whole body moisturizing crème with natural vegetable oils which is absorbed quickly. In this embodiment, the composition contains the amide (the second reaction product) and/or the third reaction product (ether-ester) as the carrier in carrier effective amounts in combination with the moisturizing crème in moisturizing effective amounts in a cosmetic composition. Preferably, the aromatic amide to aliphatic molar ratio ranges from about 1 to about 6, more preferably, from about 1 to about 4 and most preferably from about 1 to about 3. The molar ratio of the aliphatic amide (second reaction product) to the third reaction product is preferably about 1:1 and more preferably from about 1 to about 2 and most preferably about 1 to about 4. In moisturizing creams, it is important to have an occlusive outer layer. Optionally, the occlusive outer layer also include a layer that provide a soft silky hard feel. The occlusive layer can be a mineral oil, but it is more preferably beeswax or providone, especially PVP. The amide is present in amounts ranging from about 0.5% to about 1.5% by weight of the composition. The second reaction product tends to emulsify and transport the vegetable oils transdermally through the skin.

In another embodiment, the transdermal composition transports an active ingredient through the epidermis and deposits it in the dermis. An example of such a product is an antimicrobial moisturizing crème. For example, goldenseal is a natural herb that is widely used as a natural antimicrobial compound, particularly useful against yeast. In a product designed to protect the bottom skin of incontinent adults, goldenseal is transported through the epidermis into the dermis. As the outer skin is worn away and sheds, the dermal skin becomes epidermal skin. Typically, the goldenseal is first implanted in the dermis, but over time, it moves to the epidermis then to the skin surface. Those skilled in the art will recognize that any number of different compounds, natural or artificial can be transported as goldenseal in said embodiment. However, the present invention is directed to the transdermal composition comprising the second product (amide) or hydrate in carrier effective amounts as defined hereinabove and pharmaceutically effective amounts of the goldenseal or equivalent. Preferably, the second reaction product (amide) or hydrate is present in an amount ranging from about 0.1% to about 1.5% by weight of the composition, and more preferably from about 0.3% to about 1% by weight of the composition and most preferably from about 0.5% to about 0.7% by weight of the composition. Thus, the composition contains the amide in carrier effective amounts. The composition containing the amide permits the composition to penetrate through the dermis.

As another example, PABA is a well known sun screen compound. An embodiment where PABA is transported into the dermis would make a product that provided all day sunburn protection without recoating the skin. Such composition would contain the amide as the carrier in carrier effective amounts as defined herein and ether-ester in amounts sufficient to transport the sunscreen compound to the dermis together with the PABA in sunscreening effective amounts, as e.g., amounts found in commercially available sunscreens. Preferably the amide is present in amounts ranging from about 1 to about 10% by weight of the composition and more preferably from about 1 to about 7% by weight of the composition and most preferably from about 3% to about 6% by weight of the compositions. Preferably the amide to ether-ester molar ratio is about 1.

The same principle works with hair. It is straightforward to envision hair conditioner and hair colorants as being transported into the hair follicle. Less obvious is the possibility of transporting color into the roots of the hair such that the colored hair grows out with the new color. The cosmetic composition of the present invention contains the ether-ester and/or the amide and/or hydrate in carrier effective amounts, as defined here in combination with the hair conditioner in hair conditioning effective amounts, as found in hair conditioning products and/or hair colorants in coloring effective amounts, as e.g., found in commercial products. Preferably the ether-ester and amide and/or hydrate are present in amounts ranging from about 3 to about 10% by weight, and more preferably from about 4 to about 7% by weight of the composition.

The aromatic amide or hydrate with $R_7$ is an anti-microbial compound. When mixed with fatty acids and soaps, a bar soap can be produced with residual anti-microbial activity. The aromatic amide and/or hydrate penetrates the SC and binds the anti-microbial moiety to the surface of the skin. The anti-microbial activity remains on the skin surface until it is naturally sloughed off. The same strategy works in a variety of skin care products, such as antiperspirants and antiseptic hand washes. The aromatic tertiary amide (that is, a tertiary amide with $R_7$ present) or hydrate thereof is present in an amount ranging from about 0.1% to about 1% by weight of the transdermal composition, and more preferably from about 0.5% to about 0.7% by weight of the composition.

The aliphatic amide containing fatty groups as defined herein, or hydrate thereof is useful as a shaving cream. The tertiary amide and/or hydrate binds to the skin and leaves a protective fatty layer on the surface. The razor glides over the surface without making nicks or cuts.

Consequently, it is preferred that the composition is prepared as shown by this exemplary procedure. It is to be noted that this procedure is illustrative.

The quaternary ammonium salt and fatty acid are placed in water optionally in the presence of an organic base in a mole ratio ranging from about 1 to about 10 and about 10 to 1 and more preferably about 1:6 to about 6:1 and most preferably at about 2:1 to about 1:2 at a pH less than 4.5. The reaction is allowed to proceed for a proscribed length of time for product to form (less than the time to convert the maximum amount of product). Preferably, the reaction proceeds for less than one hour and more preferably less than 30 minutes and most preferably less than 15 minutes. The fatty alcohol and the monoglyceride are next added to the reaction and the mixture is allowed to stand preferably, with continuous stirring, for sufficient amount of time for the pH to stabilize and for the ether-ester to form. Preferably, the mixture is allowed to stand for at most 2 hours, and more preferably at most 50 minutes. The molar ratio of organic base to the quaternary ammonium salt is about 0.01 to about 5, preferably about 0.5 to about 1 and more preferably 0.06 to about 2 and most preferably from 0.07 to about 1. The base is added thereto and the reaction is allowed to stand until the pH stops increasing (at least about 10 minutes). Preferably, the organic base is introduced into three separate additions. The first addition is added concurrently with the quaternary ammonium salt wherein the viscosity is lowered so that a gel is converted to a fluid. The second addition of organic base is added subsequent to the completion of the formation of the ether-ester. In this procedure, gas evolution occurs during the ensuing ten minutes. When the gas evolution substantially ceases, the amide reaction is complete. The pH of the resultant fluid is first increased, then slightly lowered; so a third addition of organic base is added to raise the pH to near neutral, so that the total molar concentration of base present after the third addition is at least equal to the amount of quaternary ammonium salt added. Other components normally found in pharmaceutical compositions or cosmetics are added. Then additional organic base is optionally added in amounts effective to effect phase stability. Then processing aids, e.g., surfactants, emulsions and the like are added and then heat labile ingredients are then added.

Povidone iodine may additionally be added to any of the aforementioned compositions in amounts effective to impart an anti-microbial benefit to the compositions. Preferably, it is present in an amount ranging from about 3% to about 15% by weight of the composition and more preferably from about 5% to about 10% by weight of the composition and most preferably from about 6% to about 8% by weight of the composition. It is usually added to a gel comprising the tertiary amide and the other components of the composition after the gel has cooled. Then the povidone iodine is mixed with the gel to form a stable cream.

The components of the transdermal composition of the present invention, as defined herein, when mixed in effective amounts, form emulsions. It is to be understood that in each of the compositions of the present invention the components are added together in water in amounts effective to form an emulsion.

In a preferred embodiment of the present invention, the components, are mixed together to form a microsphere. The microsphere can be prepared by art recognized techniques. However, in a preferred embodiment, the fatty acid, the quaternary ammonium salt, optionally in the presence of a catalytically effective amount of the nitrogen base at a pH less than 4.5 at a temperature greater than the melting point of the fatty acid, e.g. 60° C. and the active ingredient, optionally the fatty alcohol, and the monoglycerol fatty ester and any other optional additional components found in topical pharmaceutical compositions or cosmetic compositions are mixed together in water in amounts effective to form an emulsion, and the emulsion thus formed is sheared under effective conditions to form a microsphere. More preferably, the mixture is sheared with an Admix Rotasolver™ agitator (Admix, Inc. 23 Londonderry Road, Londonderry N.H., 03053) at a shear rate greater than the Critical Shear Ratio.

Typically, when stirring a mixture containing a surfactant such as a quaternary ammonium salt, the mixture goes through a shear thinning region at a tip speed ranging from about 50 in/see to about 60 in/sec, wherein tip speed is calculated as the product of agitator diameter and agitator speed in revolutions per minute.

The transition is essentially linear between 50 and 60 in/sec. As the tip speed increases beyond 60 in/sec, the energy to turn the agitator increases. The tip speed where the shear thinning takes place is called the Critical Shear Rate.

Fatty mixtures of the present invention freeze at a temperature between 63° C. and 55° C. That is, the fat portion of the mixture changes from a liquid to a solid across the 63-55° C. temperature range. This temperature range is called the Freezing Zone. Other ingredients freeze at lower temperatures.

When the mixtures of the present invention are sheared at a shear rate greater than the Critical Shear Rate as the mixture cools through the Freezing Zone, a unique structure is formed. Under a microscope, these microcrystalline structures form spheres. The faster the transition through the Freezing Zone, the smaller and more uniform the sphere structure.

Preferably, a quantity of ambient water sufficient to lower the mixture temperature to a temperature just below the Freezing Zone is added as a water quench when the mixture temperature is just greater than the highest temperature in the Freezing Zone, meanwhile mixing at a shear rate greater than the Critical Shear Rate.

More preferably, it takes about 24% of the final batch weight of 20-25° C. water to cool the mixture from 63° C. to about 53° C.

The various transdermal compositions of the present invention can be processed into microspheres. The microspheres contain the active ingredient. While one skilled in the art would expect small crystals during high shear freezing of non-fatty materials, the transdermal compositions of the present invention surprisingly form spheres that are visible at 1,000× magnification.

Even more surprising is the impact these small spheres have on the active agents. For example, benzethonium chloride is the active ingredient in first aid antiseptic over the counter (OTC) products at a concentration between about 0.1-0.2% (w/w). Benzethonium chloride is a reactive material that is unstable in an acid environment; it reacts with fatty acids and soaps and thus is unstable. Thus, if added to the transdermal compositions of the present invention which is then processed into a microsphere, it would be expected that the compositions would be unstable. However, it is just the opposite.

When benzethonium chloride is added in therapeutically effective amounts to the mixtures described herein, it is stable if added at ambient temperature at a pH greater than 6. On the other hand, it is not stable if added at temperatures below the Freezing Zone and above ambient temperature at a pH of about 7.5 to about 8. Surprisingly, benzethonium chloride is stable if added at a temperature above the Freezing Zone with a tip speed greater than the Critical Shear Rate at a pH of about 7.5 to about 8.

Thus, it is advantageous to add benzethonium chloride at a temperature greater than the Freezing Zone because benzethonium chloride acts as a preservative against microbial growth during slow cooling to ambient. During cooling, pools of condensate accumulate on the nutrient-rich surface of the mixture. Without a functioning preservative, microorganisms can thrive at the interface between condensate and nutrient-rich mixture. With a functioning preservative, the microorganisms are inhibited from growing.

Thus, an embodiment of the present invention comprises the various transdermal compositions described herein containing a preservative such as benzethonium chloride in an amount effective to prevent or retard the growth of microbes processed into a microsphere, as described herein.

These transdermal compositions may additionally contain active ingredients described hereinbelow.

As one skilled in the art can well appreciate there are endless numbers of combinations that can be made to create the desired skin effects. For example, when the quaternary ammonium salt, such as dimethyl distearyl ammonium chloride (DDAC), and the like, is present in a neutral pH in the first transdermal composition of the present invention described hereinabove, the formic acid from the bug bite is more effectively and more rapidly neutralized. On the other hand, when the quaternary ammonium salt, e.g., DDAC, is present in the seventh transdermal composition of the present invention, the healing rate on open wounds improves. However, when the quaternary ammonium salt, e.g., DDAC, is not substantially converted to the first reaction product, some of the patients, approximately 25% thereof, feel pain. But, when the quaternary ammonium salt, e.g., DDAC, is split between the first reaction product (80%) and the unreacted DDAC (20%), rapid healing is observed and the patients did not feel pain.

If cetyl alcohol is additionally present, when it is present in the acid reaction zones, the pain is mitigated, however, when present in the neutral zone the detergency of the formulation increases.

Another embodiment of the present invention relates to a combination product, i.e., compositions containing one or more of the following: the quaternary ammonium salt, fatty acid, fatty alcohol, nitrogenous base, monoglycerides, the first reaction product, the second reaction product, the third reaction product and the fourth reaction product. Examples of these are exemplified in Examples 17-24. It is preferred that such combinations include at least one of the carriers described hereinabove.

In an example, these combination products can be used as a moisturizing skin product and barrier product, as for example, in maintaining skin health.

Maintaining skin health is always complex, particularly with hands that are exposed to harsh chemicals. For example, health care workers and workers in the food manufacturing and food handling business are always washing their hands and sanitizing them with iodine or >62% alcohol. Treatment with antiseptic products tends to cause cracking and chaffing of hands (contact dermatitis). Hands that are cracked can harbor microorganisms in the cracks. It is difficult to kill these hidden microorganisms because the antiseptic fluids cannot get into the cracks and crevices during the sanitizing process. Thus the hands emerge from the sanitizing process with viable organisms which can grow out to meaningful populations between sanitizing treatments.

Other workers use their hands with aggressive chemicals. Workers in the chemical industry and workers in the beauty care industry stress the health of their skin by handling the normal chemicals inherent in doing their job. These hands are often cracked and chapped. The antiseptic nature of the hands is typically not critical, but cracked and chapped hands hurt. This is particularly true for beauty care workers whose motor skills are crucial to their jobs.

Ingredients that are necessary for healthy hands should be rapidly absorbed by the skin. Antiseptic ingredients should not be absorbed by the skin. A barrier product to keep noxious chemicals away from the skin should not be absorbed.

It is difficult to make a skin care product that is simultaneously absorbing and not absorbing. In a situation where the skin requires an absorbing technology and a non absorbing technology, more than one application is required.

The prior art deals with this problem by using a moisturizing crème followed by an antiseptic or a barrier crème. This solution can make the hands feel better, but the secondary treatment of either sanitizing or providing a barrier is compromised because the moisturizing ingredients in the first application remain on the surface of the skin. The surface oils cover and protect the microorganisms, such that the expected sanitizing is compromised.

Likewise with a barrier crème, the barrier cannot attach to the skin because there is an intermediate level of moisturizing oil between the skin and the barrier.

This dilemma is solved by having a transdermal first application. With a mixture such as the fourth transdermal composition described herein containing nutrients, as disclosed herein, especially olive oil, (preferably about 5.3%), the composition is transdermally delivered to the subsurface skin. Along with other transdermal nutrients, the interior skin is fed and strengthened. Importantly, the surface is substantially dry and prepared for a second application.

In an embodiment, the second application is the antiseptic mixture previously disclosed hereinabove.

In another embodiment, barrier film forming compounds are added to the seventh transdermal composition, as described herein. A preferred embodiment is exemplified in Example 20 hereinbelow, except that Cetyl Alcohol is 3.82%. Furthermore, said barrier film compounds are added in amounts effective to form a barrier film, said barrier film forming compounds are added after the quench water has dropped the temperature below the Freezing Zone in the formation of the microspheres. This technique removes the barrier compounds from the microcrystalline sphere formation.

Examples of barrier film forming compounds are:

Waxenol 822—arachidyl behenate, Polyderm PE—poly diethyleneglycol adipate/IPDI copolymer, Polyderm CO—castor oil/IPDI copolymer, Monoderm I-20—octyl dodecanol dimer with IPDI, Polyderm SA—dimethiconol DI-PEG 2 soyamine/IPDI copolymer, Monoderm I-16—isocetyl alcohol dimer with IPDI, all of which are sold by Alzo International, Inc.

The barrier mixture can be used alone or as a second product following a transdermal moisturizing treatment.

One skilled in the art will recognize that alternate barrier compounds are possible as well as varying the relative amounts of the listed barrier compounds. In the present invention, the skin is protected using a transdermal composition followed by a non transdermal composition.

The transdermal compositions of the present inventions can be a pharmaceutical composition or cosmetic composition. The topical compositions may be in a number of common forms typically of topical formulations, e.g., hydrophilic lotion, an ointment, cream, gel, sprays, salves, jellies, pastes, syrups and the like. They may include one or more other formulation additives typically found in cosmetic or pharmaceutical compositions.

It is preferred that the transdermal compositions are provided with a liquid carrier although they may be carrier free. This liquid carrier is any liquid which the liquid carrier for the composition can also vary. Indeed, any carrier that does not substantially interfere with the components or the function of the components, and which allows a film to form and thereby exclude the carrier from the skin surface as it evaporates, is suitable. Exemplary carriers include water, and lower molecular weight alcohols such as ethanol, isopropyl alcohol, sec-butyl alcohol, glycerin, and propylene glycol, although water is generally preferred for the particular ingredients described in this document. Alternatively, the carrier may be one of the carriers identified hereinabove. In another embodiment, the carrier may be a combination of any of the above.

The composition may comprise one or more active agents, which are chosen based upon the properties that one desires from the composition. For example, in one embodiment the composition may include an aggressive cleansing or skin preparation ingredient. Such active agents cleanse the surface of the skin immediately upon application of the composition to the skin, and cleanse the skin sufficiently before a film is formed from the first film forming component, and before the first film forming component excludes the active agents from the surface of the skin.

As an active agent the composition may contain cleansing ingredients capable of removing microbials, viruses, and other foreign contaminants from the surface of the skin. Cleansing ingredients may also be capable of scouring dead and dying layers of skin from the skin surface. The cleansing ingredient may suitably comprise non-ionic surfactants because: (1) this class of compounds readily cleanses the skin, and removes the fatty dead, and dying layers of the outer surface of the skin (the stratum disjunction and stratum corneum); (2) this class of compounds is typically very soluble in the water base of the composition; (3) this type of compound is an effective antiviral compound; and (4) this class of compounds allows the proper functioning of the other active ingredients of the composition.

Surfactants may also be present as a processing and/or as active agent. As an active agent, they are particularly suitable because of their ability to cleanse at the interface of the liquid composition and the outer layers of the skin. A particularly suitable nonionic surfactant is sold under the trademark Triton X-100, and comprises octoxylenol, most suitably having 9-10 repeating units of ethoxylation. Another particularly suitable nonionic surfactant is nonoxynol-9, which can be used alone or in combination with other surfactants.

Suitable anti-microbial and cleaning active agents that can be used as active agents or as additions can be incorporated into the composition include propylene glycol, berberine sulfate, various quaternary ammonium compounds, such as dimethyl benzethonium chloride, benzalkonium chloride, benzethonium chloride, and cetyl pyridinium chloride. Additional antimicrobial and cleansing agents include, but not limited to parachlorometaxylenol, nonoxynol-9, chlorohexadine gluconate, and lauricidin (glycerol monolaurate). Other active agents include skin healing emollient ingredients such as allantoin, aloe, dimethyl sulfone, dimethicone, fragrances and anti-oxidants.

It is also possible to include active agents with medicinal properties in the composition which, when delivered topically, are absorbed by the skin and metabolized. Any active agent that is fat or water soluble, or which can be rendered fat or water soluble, is a suitable candidate for delivery through the compositions of the present invention, because such agents are capable of migrating through the final film formed by the composition, and thereafter being topically delivered to the skin.

An example thereof is the transdermal composition of the present invention in association with a herb, such as the fourth transdermal composition described hereinabove. The herb may be present as a complete extract or a fraction thereof. Many herbs are functional active ingredients, but are digested when entering the body via the stomach. However, when the active herbal extracts are delivered to the skin topically in association with a transdermal composition of the present invention, the herb can act on the targeted site on the skin, without being digested. For example, when the herb extracts is present in the transdermal composition of the present invention, it was effective in treating skin cancer if present in cancer treating effective amounts, retarding the growth of the cancer cells or killing the cancer cells.

The medicinally active agents of the invention can be added singly, or in any combination. Each medicinally active agent typically comprises from about 0.01 weight % to about 95% and more preferably about 30 weight percent of the composition, although active agents can be present, either singly or in combination, in quantities as high as about 35 wt. %, about 20 wt. %, about 15 wt. %, about 10 wt. %, or about 5 wt. %. Most medicinally active agents as defined by the FDA are preferably present from about 0.01 weight % to about 5:0 weight percent. Preferred medicinally active agents, not defined by the FDA, include alkylglycerols, alkoxyglycerols, polyunsaturated fatty acids or polyunsaturated oils, fat soluble vitamins, sulfur compounds, minerals, antioxidants, amino acids, energy stimulators, steroidal hormones, or glycoprotein hormones. Preferred medicinally active agents also include a variety of other healing agents including glycyrrhizic acid, ribonucleic acids, aloe vera, allantoin, bioperine, berberine hydrochloride, colostrum, dexpanthenol, glucosamine salts, inositol, phytantriol, pyrrolidine carboxylic acid, jojoba oil, symphytum officinal, polysorbate 80, vanilla extract, and adducts of a nitrogenous organic base and a fatty acid. Adducts of nitrogenous organic bases and fatty acids are especially appropriate for use in higher concentrations.

Glycerides, including mono-, di-, and triglycerides, and alkoxyglycerols and alkylglycerols, are particularly suitable as active agents, or as carriers for active agents, in topical applications. These components have independent medicinal properties, are capable of independently migrating through the film, and can also solubilize other fat soluble active agents and carry them through the first film to the surface of the skin. Particularly suitable glycerides typically comprise from about 10 to about 36 carbon atoms, can be conjugated or saturated, and are generally liquid at room temperature. Preferred glycerides include, lauricidin, vitamin D suspended in palm oil, conjugated linoleic acid ("CLA"), gamma linolenic acid ("GLA"), and eicosapentaenoic acid (EPA). Highly unsaturated oils are also especially suitable active agents in such topical applications because such oils have an antioxidant benefit when applied to the skin, and in addition they are effective transport vehicles for fat soluble active agents.

The polyunsaturated fatty acids used as medicinally active agents include conjugated linolenic acid, alpha-linolenic acid, alpha-linoleic acid, gamma linolenic acid, dihomo-gamma-linolenic acid, docosahexaenoic acid, eicosapentaenoic acid. The polyunsatured fatty oils useful in the invention include neem oil, shark liver oil, lemon oil, or squalene. Other fatty oils include lemon oil and squalane. Shark liver oil and for neem oil are typically used at higher concentrations than other medicinally active agents, and are thus typically present at concentrations of up to 10, 5, or 3 wt. % of the composition.

Preferred fat soluble vitamins include vitamin A, vitamin D, vitamin E, vitamin K, a tocotrienol, lycopene, b-carotene, ascorbyl palmitate, and luteine. Preferred sulfur compounds include dimethylsulfone, zinc sulfate, or lipoic acid. Preferred minerals include zinc sulfate; zinc 1-monomethionine; and compounds of copper, calcium, magnesium, chromium, selenium, vanadium, cobalt, and silica. Compounds include salts and chelates, among others, and especially include calcium proprionate; copper porphyrin compounds, silicic acid or silica gel, and copper-curcumin.

Preferred anti-oxidants include ascorbyl palmitate, neem oil, squalene, ferulic acid, lipoic acid, grape seed extract, boswellin, and bilberry extract. Preferred amino acids include arginine, praline, glutamine, glycine, or trimethyl glycine, ornithine alpha-ketoglutarate, and 1-pyrroglutamic acid.

Energy stimulators may also be active agent. These are defined as compounds that provide easily metabolized sources of energy for the synthesis of ATP, and include bee pollen, natural honey, forskholin, and arginine. Preferred steroid hormones include cortisol, pregnenolone, and dehydroepiandrosterone.

Another class of active agents include optically fluorescent or phosphorescent compounds or compositions that can absorb ultraviolet light and re-emit it as visible light. When hands or other skin surfaces that have been treated with the resulting fluorescent or phosphorescent compositions, exposure to a source of ultra-violet ("black") light can be used as a method to check for the presence of the composition on the skin. This property might be particularly useful in skin cleaning and/or skin protecting compositions utilized in hospital, food manufacturing, or food service facilities, as a means for easily checking for the presence of the cleaning or skin protecting composition.

As stated above, the transdermal compositions of the present invention include new components that are new compounds. The first of these is the compound which is the reaction product of a quaternary ammonium compound and a fatty acid. This reaction occurs in an aqueous solvent at a temperature greater than the melting point temperature of the quaternary ammonium compound over a time period long enough for the reaction mixture to reach a substantially constant pH which pH is less that the pH of any single reactant present in the reaction mixture when measured alone in water.

An example of this reaction to produce the new compound, dimethyl distearyl ammonium stearate, involves reaction of the quaternary ammonium compound, dimethyl distearyl ammonium chloride, with the fatty acid, stearic acid, infra.

A second new compound employed in the transdermal compositions of the present application is the reaction of the first reaction product with a catalytically effective amount of nitrogenous organic base. This class of new compounds is illustrated by the reaction of dimethyl distearyl ammonium stearate in the presence of an effective amount of nitrogenous organic base, e.g., triethanolamine, wherein the reaction occurs at the conditions present at the time when the first reaction product was formed. This reaction product is an amide.

A third new compound is denoted as the third reaction product. That product is the reaction product of a first reaction between a fatty acid and a fatty alcohol in acid to form a fatty ester and a second reaction between the fatty ester and a monoglyceride. An example of that new compound is the product formed by the stepwise reaction of the fatty alcohol, e.g., cetyl alcohol, and the fatty acid, e.g., stearic acid, and then the monoglyceride, glycerol monolaurate. This reaction, which occurs under acidic conditions, produces the reaction product compound cetyl glycerol laurate.

The various transdermal compositions described herein are applied topically to the skin of a patient. In the present invention, the patients to whom the transdermal applications are applied are mammals. Examples of mammals who can benefit from application of the transdermal compositions thereto include dog, cat, horse, pig, cow, donkey, monkey, humans, and the like. The most preferred mammal is human.

It is to be understood that the transdermal compositions of the present invention are applied topically to the skin. Moreover, the transdermal compositions of the present invention may be carrier free, although it is preferred that a carrier typically used in the pharmaceutical arts or cosmetic arts or a carrier described hereinabove, such as the second reaction product or third reaction product or fourth reaction product, be the carrier associated with the pharmaceutical agent.

The present invention includes kits which encompasses the aforementioned transdermal compositions, and portions thereof. That is, kits within the scope of the present invention comprise complete components of each of the transdermal compositions, components that comprise the compositions without the active agents and/or liquid carriers and the like. For example, the kit may contain one container containing the carriers identified herein and the other container containing the active agent.

As used herein, the plural denotes the singular and vice versa. Unless indicated for the contrary, the percentages are by weight.

In addition, the term "saturated" and "unsaturated" refers to the number of carbon-carbon double bonds. If a fatty acid or alcohol is saturated or completely saturated, this denotes that the fatty acid or alcohol contain no carbon-carbon double bonds; if on the other hand, the fatty acid or alcohol is unsaturated then it is to be understood that it contains at least 1 carbon-carbon double bond.

The abbreviation TEA refers to triethanolamine.

Moreover, unless indicated to the contrary, the term "amide" refers to the second product, or hydrate as defined herein.

Further, unless indicated to the contrary, the term salts of a fatty acid or synonym thereto refers to a pharmaceutically or cosmetically acceptable salt thereof.

As used herein, the term aliphatic tertiary amide or aliphatic quaternary salts or equivalents thereto refers to tertiary amide or salt, respectively containing only aliphatic moieties thereon in the absence of aromatic moieties.

The term aromatic tertiary amides or aromatic quaternary salts or equivalents thereto refers to a tertiary amide or quaternary salt respectively, which has at least one group thereon containing an aryl moiety as defined herein, e.g., aryl group, aryl alkyl group or $R_7$.

The term treating refers to management and care of a mammalian subject for the purpose of combating disease, condition or disorder by administering a pharmaceutical composition as defined herein topically to the skin, and promoting the healing thereof or alleviation of the symptoms associated with the disease, condition or disorder.

The process for making tertiary amides is illustrated in the Examples and is now described generically:

1. Water, quaternary surfactant and fatty acid are heated together at a temperature greater than the melting point of the fatty acid with gentle stirring for a time long enough to enable gas to form and dissipate. The pH drops below the pH of either component-in-water alone before the gas release occurs. Optionally, small amounts of nitrogenous base, e.g., TEA can be added such that the resulting pH is less than about 6. Base, such as TEA reduces the tendency to form gels. Too much base, e.g., TEA raises the pH above 6.

2. The pH of the mixture can be rapidly increased by the addition of a base. The rate of pH-increase is reduced significantly when the base-to-fatty acid molar ratio is greater than 1 (which excess quaternary surfactant). The rate of pH-increase is reduced significantly when the base-to-quaternary molar surfactant ratio is greater than 1 (with excess fatty acid). The rate limiting component defines the inflection point where the rate of pH-increase slows.

3. Aliphatic quaternary surfactants mixed with fatty acids release gas more slowly than aromatic quaternary surfactants and are more likely to form gels. Gel formation inhibits gas release. High shear mixing in the presence of released-not-yet-dissipated gas forms gels that inhibit gas release. Aliphatic quaternary surfactants and fatty acid do not release gas at a pH greater than about 6.

4. A particularly effective way to prevent gel formation is to add quaternary surfactant to fatty acid in steps. The gas release begins after the first step, then dissipates. The nest step of quaternary surfactant is added, a weak gel may be formed, but more gas is released and dissipates. The gel breaks when the gas is dissipated. The total about of gas release is greater when partial quaternary surfactant additions ate made slowly rather than adding all the quaternary surfactant at once.

5. If a gel forms a gas release substantially stops, the gbas release can be restarted by diluting the reaction mix with water. The optimum gas release temperature is about $80\pm10°$ C. Gas release time for aliphatic quaternary surfactants is about 60 minutes @ 80° C. Gas release time for aromatic quaternary surfactants is about 30 minutes @ 80° C. If the fatty acid is in molar excess, the gas release is faster. If the quaternary surfactant is in molar excess, gels may form. Aliphatic quaternary surfactants are more likely to form gels than aromatic quaternary surfactants.

6. Aromatic quaternary surfactants, mixed with fatty acids at a pH greater than 6, release gas. The rate of release is slower at higher pH. The ideal pH is less than 4.5. The gas release takes place at ambient temperature if the fatty acid is liquid at ambient temperature.

7. Aromatic quaternary surfactants will release gas with unsaturated fatty acids in the present of an assortment of other compounds; aliphatic quaternary surfactants do not release gas when mixed with, for example, calcium-containing compounds. For example, in Example 20, if the benzethonium chloride is added at a temperature less than the freezing point of the saturated fatty acid (e.g. <55° C.0, thee is an immediate rise in the level of the processing vessel and an endothermic temperature drop. It is believed that the benzethonium chloride is endothermically reacting with the various unsaturated fatty acids and releasing gas (the saturated fatty acids cannot react because the temperature is less than the freezing point of said saturated fatty acids; the release gas is entrained and reduces the specific gravity of the mix.) Example 20 contains aloe, a calcium-containing compound.

8. When the fatty acid and quaternary surfactant are first heated in water, the pH drops below 5. If fatty alcohol and glycerol esters are mixed together, the pH rises and falls cyclically. After about one hour @ 80° C., the pH fluctuation substantially stops.

The following non-limiting examples further illustrate the present invention.

EXAMPLE 1

Formation of Distearyl Stearamide and Cetyl Glycerol Laurate

An equimolar mixture of stearic acid and dimethyl distearyl ammonium chloride (DDAC) was dissolved in water in the presence of triethanolamine (TEA) wherein the TEA was present such that the mole ratio of DDAC to TEA was 10:1. The aqueous mixture was maintained at a temperature in excess of 60° C. and at a pH in the range of from about 3 to about 5.

The reaction proceeded with the evolution of gas. The pH of the reaction mixture was measured during this reaction. The pH dropped exponentially from a pH in the range of 5 to 6 down to a pH of 2 to 3 within 5 minutes. This is quite remarkable insofar as the pH of stearic acid in water is about 4.5 and the pH of DDAC is about 6.

Cetyl alcohol and glycerol monolaurate were thereupon added to the reaction mixture in a concentration of 4 moles of each of these compounds per mole of DDAC. Gellation and subsequent creaminess occurred. The reaction mixture was unchanged for 75 minutes. Subsequent to the aforementioned 75 minute reaction time, TEA was added in an identical concentration as the first addition of TEA, that is, one mole of TEA was added to the reaction mixture for every 10 moles of DDAC present therein. The second addition of TEA resulted in further gas evolution. This reaction was allowed to continue for 10 minutes.

A third charge of TEA was introduced into the reaction mixture to bring the total TEA concentration equal to the molar concentration of the DDAC to bring the total such that the pH of the reaction was greater than 6.

The reaction was stopped by addition of the dimethylation inhibitor, aloe vera (0.25%, by weight based on total reaction mixture).

EXAMPLE 2

Formation of Dimethyl Distearyl Ammonium Stearate (DDAS) and Cetyl Glycerol Laurate Example 1 was repeated but for the absence of TEA from the equimolar mixture of stearic acid and DDAC and from the addition of cetyl alcohol and glycerol monolaurate. Instead, an amount of TEA, equal to the total amount added in Example 1, was added at the time of additions of TEA in the third charge in Example 1.

EXAMPLE 2A

Formation of DDAS and Cetyl Stearate

Example 2 was repeated but for the sequence of addition of glycerol monolaurate. Instead of being added with cetyl alcohol, an equal amount of glycerol monolaurate utilized in Example 2 was added after the addition of the TEA.

EXAMPLE 2B

Formation of DDAS and Triethanolamine Stearate (TEAS)

Example 2A was repeated but for the sequence of addition of glycerol monolaurate and cetyl alcohol. Instead of being added in the second step, after the equimolar mixture of stearic acid and DDAC, the same amount of the glycerol monolaurate and cetyl alcohol added in Example 2 was added after the addition of TEA.

EXAMPLE 2C

Formation of DDAC and TEAS

Example 2B was repeated but for the addition of DDAC prior to addition of TEA. Rather, an equal amount of DDAC added in Example 2B, was added concurrently with the addition of glycerol, monolaurate and cetyl alcohol.

EXAMPLE 2D

Formation of Distearyl Stearamide (DSS) and Cetyl Stearate

Example 1 was repeated for both the sequence of addition of glycerol monolaurate. The glycerol monolaurate added in Example 1 concurrently with cetyl alcohol, was added subsequently to the third addition of TEA.

EXAMPLE 2E

Formation of DSS, Cetyl Glycerol Laurate and Cetyl Stearate

Example 1 was repeated but for the mole ratio of stearic acid and DDAC. Whereas the mole ratio of stearic acid to DDAC in Example 1 was 1:1, the mole ratio of stearic acid to DDAC was 2:1. In addition, the molar ratio of glycerol monolaurate to cetyl alcohol, which was 1:1 in Example 1, was 0.5:1.

EXAMPLE 2F

Formation of DSS, Cetyl Glycerol Laurate and TEAS

The process of Example 1 was repeated but for the inclusion of additional stearic acid. The stearic acid which was added subsequent to third introduction of TEA resulted in a molar ratio of stearic acid to DDAC of 2:1.

EXAMPLE 2G

The process of Example 1 was repeated, except that 0.5% aloe vera was added with the DDAC and the TEA.

EXAMPLES 3-5

Preparation of Transdermal Compositions Employing Various Fatty Acids

Example 2 was repeated employing the fatty acids; Conjugated Linoleic Acid (CLA); eicosapentaenoic acid (EPA); and gamma linolenic acid (GLA), were all dissolved in water and the pH of the resulting solutions were measured with a calibrated pH meter. These pH's are reported in Table 1.

Three solutions of DDAC (188.2 g) in distilled water (2,000 g) were contacted with masses of CLA, EPA and GLA, such that the molar ratio of DDAC to each of the aforementioned fatty acids was 1:1 at a temperature of 70° C. to 75° C. and after 10 minutes the pH of the reaction products of each of these products was measured. These results are summarized in Table 1.

TABLE 1

| Example No. | Quaternary Compd, g | pH | Reaction of Quaternary Compound with Fatty Acid, g (pH) | Product Compound | pH |
|---|---|---|---|---|---|
| 1 | DDAC, 188.2 | 5.38 | None | | |
| 2 | DDAC, 188.2 | 5.38 | Stearic, 80 g (4.81) | DDAS | 2.38 |
| 3 | DDAC, 188.2 | 5.38 | CLA, (4.00) | Dimethyl Distearyl Ammonium Linolenate (DDAL) | 2.28 |

EXAMPLES 6-9

Preparation of First and Second Transdermal Compositions Employing Various Quaternary Compounds Four quaternary compounds, dimethyl benzethonium chloride (DMBC) (27 g), monomethyl benzethonium chloride (MMBC) (19 g), benzalkonium chloride (BAC) (50 g) and Merquat 550 (96 g) were mixed with distilled water (2,000 g). Merquat 550 is a trademark owned by Calgon, Inc. its manufacturer, for a proprietary cationic polymer having a repeating unit molecular weight of 680 and an overall molecular weight of about 10,000. The pH of these first transdermal compositions were measured. The solutions were thereupon heated to 70°-75° C. and stearic acid (40 g) was added. Ten minutes after acid addition, the pH of the product composition were measured. The results of these examples are summarized in Table 2.

TABLE 2

| Quaternary Compound | pH | pH of Quat and Stearic Acid |
|---|---|---|
| DMBC | 5.02 | 3.01 |
| MMBC | 4.47 | 2.32 |
| BAC | 7.83 | 2.40 |

EXAMPLE 10

DDAC (89 g) was mixed with distilled water (2,000 g) and heated to 50° C. in a 6-quart double boiler with continuous stirring. Melted stearic acid (82 g) was added and the mixture was heated to 70° C.-75° C. for 20 minutes. Melted cetyl alcohol (105 g) was thereupon added to the mixture at 70° C.-75° C. and the mixture remained heated at 70° C.-75° C. for an additional 20 minutes. Glycerol monolaurate (79 g) was added and the mixture was heated for 20 more minutes at 70° C.-75° C. Triethanolamine (TEA) was added in an amount of 0.1 wt %, based on the total weight of the mixture, every minute. The pH of the mixture was measured after each addition of TEA.

The mole ratio of the compounds, adjusted for the purity in the raw material, specifically, stearic acid to DDAC to cetyl alcohol to glycerol monolaurate to TEA was 1:0.5:1.5:1:2, respectively.

The pH of the reaction from the beginning of the experiment as a function of time, where 0 time represents the time of initial addition of TEA, and wherein initial addition of cetyl alcohol, glycerol monolaurate and the point where the molar concentration of TEA reaches the molar concentration of DDAC are provided thereon as set forth in FIG. 1.

Analysis of Example 10

A review of FIG. 1 demonstrates that the pH of distilled water, 5.21 immediately drops after addition of stearic acid at 50° C. to about 2.36 upon reaction of DDAC therewith. This reaction generates hydrochloric acid resulting in this pH reduction. The pH then increases from 2.33 to about 2.60 upon addition of cetyl alcohol as it reacts with stearic acid. The fatty ester product of this reaction is reacted with glycerol monolaurate, a glycerol mono fatty ester resulting in a drop of pH from about 2.48 to about 2.23 insofar as this reaction effects in the regeneration of stearic acid as well as the concurrent formation of cetyl glycerol laurate. The pH rapidly rises from about 2.26 to about 6.0 as TEA is introduced. This steep increase in pH ceases at the inflection point when the molar concentration of TEA equals the concentration of DDAC, which is equal to the number of moles of hydrochloric acid generated in the reaction of DDAC with stearic acid. The slower increase in pH is a manifestation of further addition of TEA.

The two different slopes of rising pH represents the neutralization of strong acid by TEA followed by the buffering effect of the reaction mixture by TEA and DDAS.

EXAMPLE 11

Distilled water (2000 g) was mixed with DDAC (1% to 10% by wt.) and heated to 50° C. in a 6 quart double boiler with continuous stirring. Stearic acid (82 g) was added to the mixture and heated to 70° C. to 75° C. for 10 minutes. TEA was added at a rate of about 2 g/min. The pH was measured every minute. This data was plotted as in FIG. 1 depicting the data of Example 10. The inflection point between rapid and slow pH was statistically determined. These results are set forth in Table 3.

TABLE 3

| Wt. % DDAC | TEA, g Prior to Inflection Pt. | DDAS/TEA Mole Ratio at Inflection Point |
|---|---|---|
| 1 | 6 | 0.9 |
| 2 | 10 | 1.08 |
| 4 | 21 | 1.03 |
| 6 | 31 | 1.04 |
| 8 | 39 | 1.11 |
| 10 | 33 | 1.63 |

Analysis of Example 11

The number of grams of TEA added prior to reaching the inflection point increased linearly when the wt % DDAC increased from 2 to 8 wt %. The mole ratio of DDAS/TEA averaged 1.06 over this range establishing that the conversion of DDAC to DDAS, when DDAC was reacted with stearic acid, was almost complete during the 10 minute reaction period.

EXAMPLE 12

Distilled water (1,245 g) and DDAC (178 g) was heated to 50° C. in a 6 quart double boiler with continuous stirring. Melted stearic acid (164 g) was added to the distilled water. The resultant mixture was heated to 70° C. to 75° C. for 10 minutes. The pH dropped from 5.59 to 2.56. Melted cetyl alcohol (140 g) was added to the mixture at 70° C. to 75° C. and maintained at this temperature for 10 minutes. The pH increased from 2.56 to 2.62 as this reaction proceeded. Glycerol monolaurate (79 g) was added to the mixture at 70° C. to 75° C. The pH decreased from 2.62 to 2.40. During this pH reduction an additional amount of glycerol monolaurate (79 g) was added, with crude beeswax (24 g), propolis (1 g) and CLA (17 g), to the reaction mixture during the next 5 minutes. The rate of pH decline was unchanged during this period.

TEA (8.7 g) was added resulting in a pH increase to 3.5. However, the pH declined to about 3.0 over the next 20 minutes while the temperature was maintained at 70° C.-75° C. Tiny foam bubbles were noticed being released from the stirred mixture. It is theorized that these bubbles represent the release of methanol.

Figure 2:
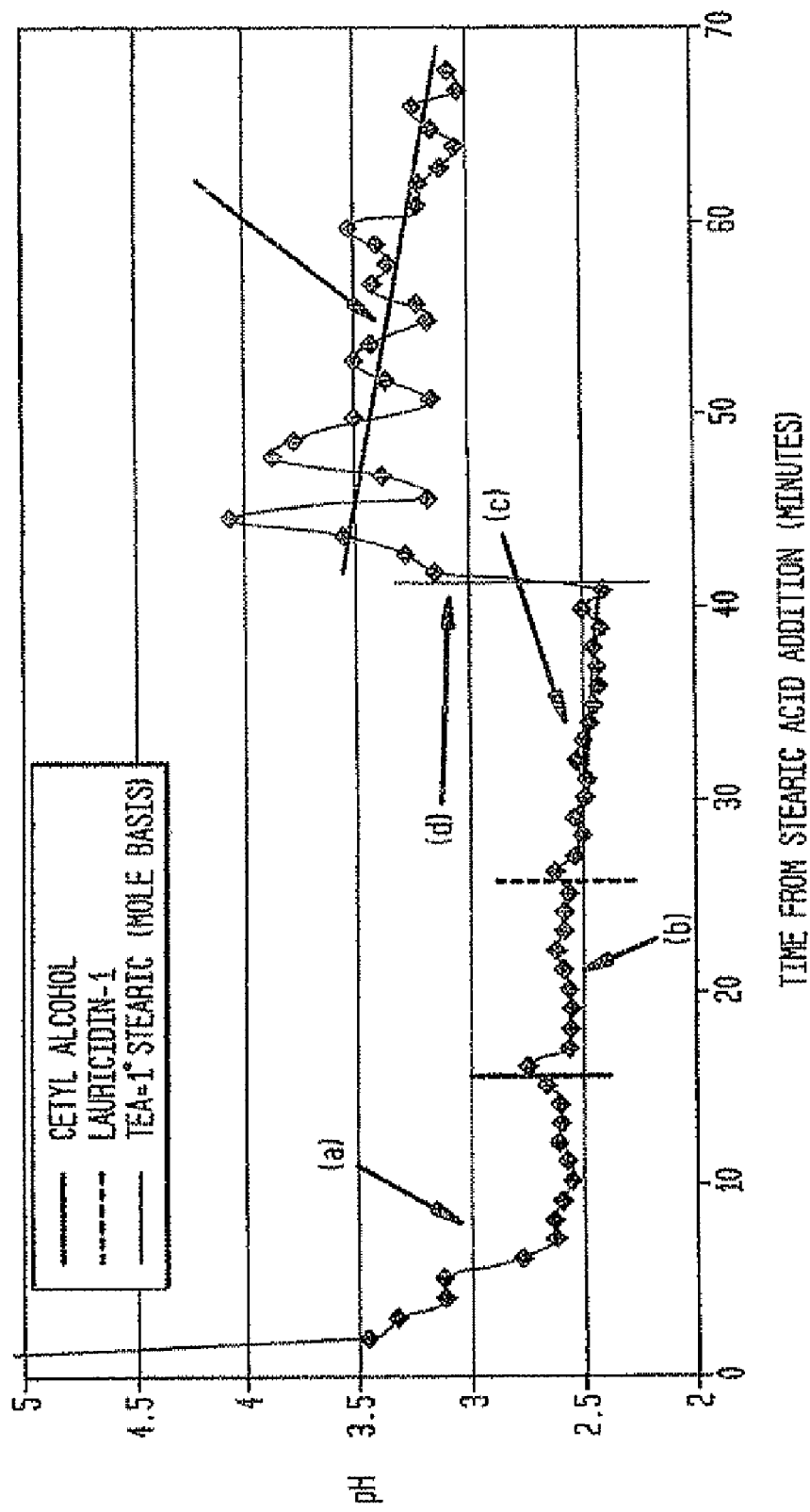
FIG. 2 is a plot of pH as a function of the time from addition of stearic acid in the reaction mixture of Example 12;
 (a) the arrow at (a) points to initial pH drop;
 (b) the arrow at (b) points to pH increase forming an ion pair;
 (c) the arrow at (c) refers to pH decline as the amide is formed; and
 (d) the arrow at (d) refers to pH increase after TEA addition.

The pH response to this experiment is depicted in FIG. 2 wherein pH of the mixture is depicted as a function of time. The pH response subsequent to addition of 0.1 mole TEA per mole of stearic acid is depicted in FIG. 2 as a converging harmonic decay. The viscosity of the mixture also dropped dramatically after TEA addition. This response is theorized to be the result of a converging harmonic decay due to competing reactions driven by the loss of stearic acid as cetyl stearate is formed (pH rises) and the gain of stearic acid as the cetyl stearate reacts with the glycerol monolaurate and regenerates stearic acid (pH falls). The pH effect from the two interdependent reactions oscillates back and forth, as first one reaction and then the other one predominates. As the reagents are consumed, the range of fluctuation declines when all the cetyl stearate and all of the glycerol monolaurate reactions are substantially complete and the pH is stabilized. That is, the reaction of DDAC and stearic acid, as well as the reaction of cetyl glycerol laurate and cetyl stearate, generate acid resulting in lower pH. The reaction of TEA with protons to form protonated TEA and the reaction of cetyl alcohol and stearic acid to form cetyl stearate both increase pH. As such, pH fluctuates. As the reactions go to completion, the fluctuations in pH are reduced. When the reactions are substantially complete the pH is stabilized.

When the pH was stable, distilled water (623 g) was added at 70° C. As illustrated in FIG. 2, no inflection point was observed. Instead, after only 5 additional grams of TEA were added, the pH gradually rose. This increased pH continued until 51 grams of TEA were added at a rate of 2 g/min. All the remaining TEA was thereupon added all at once to yield a final pH of 7.83.

Propylene glycol (3.5%) was added at 70° C. and Carbomer (0.5%) was added at 68° C. At 65° C., additional distilled water (623 g at 25° C.) was added. Agitation was increased until a smooth hand cream was obtained. Upon cooling to ambient temperature, a trained panel described the product as "drying". This drying effect was deemed the result of the formation of the tertiary amide and its partial penetration of the in the absence of an occlusive layer, such as beeswax or mineral oil. Tertiary amides open the pores of the skin, allowing moisture to leave the surface of the SC. An occlusion layer on top of the tertiary amide layer retains moisture.

EXAMPLE 13

In this example, all reactions occurred simultaneously. That is, the reactants: distilled water (2,000 g); DDAC (178 g), stearic acid (164 g); TEA (8.6 g); glycerol monolaurate (79 g); and cetyl alcohol (140 g) were added at ambient temperature to a 6 quart double boiler. TEA (8.6 g), however, added so that the molar ratio of TEA to stearic acid was 0.2:1, occurred before the addition of the glycerol monolaurate and cetyl alcohol.

Figure 3:
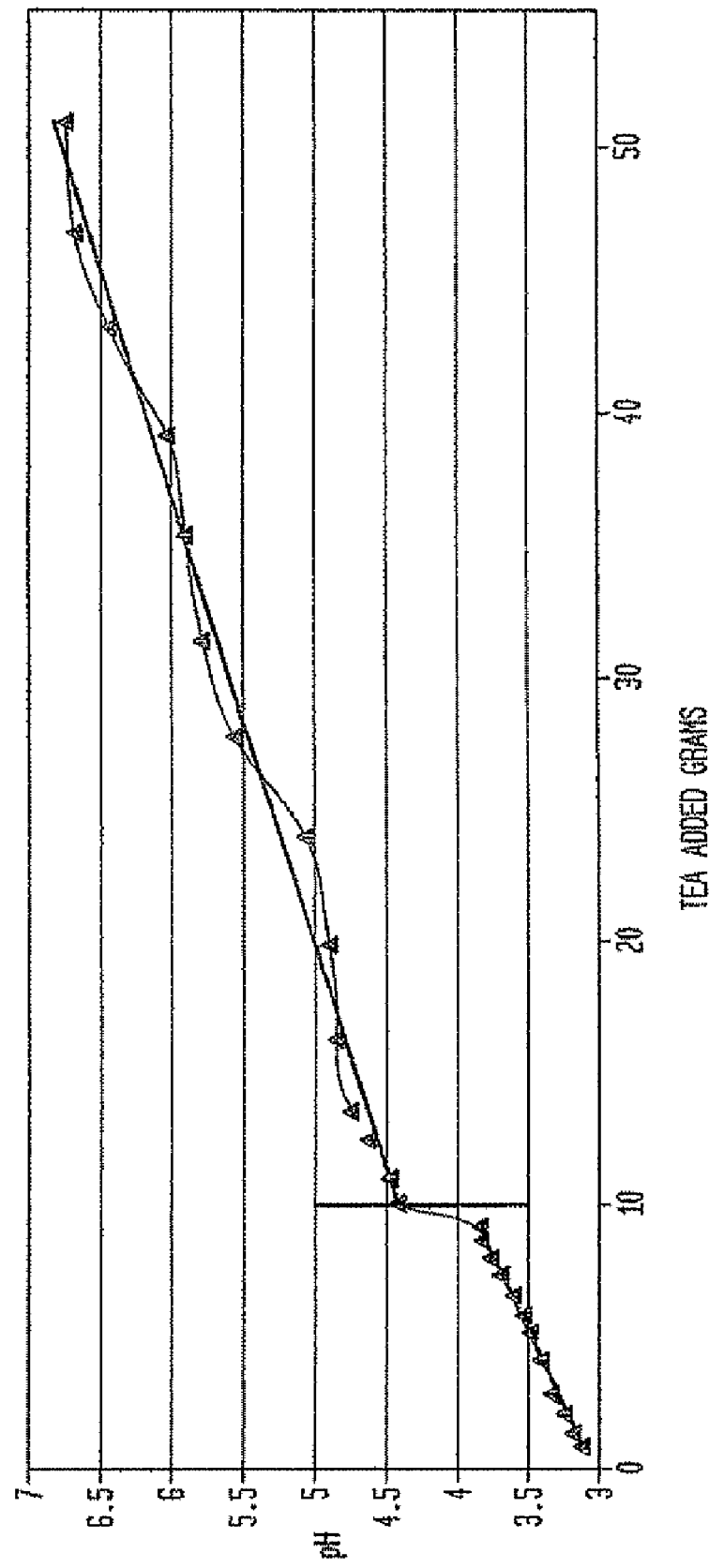
FIG. 3 is a plot of pH as a function of triethanolamine in the neutralization of the reaction mixture of Example 13. The - indicates a phase change.

The undissolved unmelted TEA-containing mixture was heated, with continuous stirring at 70° C. The pH response was an exponential decay with a slight drop in pH to about 3.12. After the reaction was allowed to react for 70 minutes, TEA was added at a rate of about 0.5 gram per minute until 9.7 grams were added. This addition is depicted in FIG. 3 wherein pH is shown as a function of TEA added. The pH response was linear up to a pH of 3.85 followed by a step increase to 4.44 coinciding with a physical phase change. Subsequent to the phase change, glycerol monolaurate (79 g), propolis (1 g), crude beeswax (24 g) and CLA (17 g) was melted and added to the double boiler along with water (623 g at 70° C.) and heated for 5 minutes. TEA (40 g) was added at a rate of 2 g/min. Additional TEA, to bring the total amount to 341 grams, was added at one time. Propylene glycol (160 g) was added at 70° C., Carbomer, e.g., Carbomer 980 (16 g), a trademark for a polyacrylic acid, owned by B.F. Goodrich, was added at 68° C. The mixture was subjected to high agitation at 65° C. to shear and smooth the emulsion.

The resulting salve, after being cooled to ambient temperature, was judged by trained panelists to be moisturizing. Glycerol monolaurate added to the acid reaction was equal to the molar amount of available cetyl alcohol. Glycerol monolaurate, added after the neutralization phase change, which occurred at a pH of 4.44, did not react with preexisting cetyl stearate. As a result, there was no free stearic acid to react with TEA and thus no TEA:stearate formed. The absence of an inflection point, as seen in FIG. 3, indicated that there was no strong acid to neutralize.

Products obtainable from variations in relative ratios and time of addition of components of Example 13 are summarized in Table 4.

TABLE 4

| Reactants | Transdermal, Moles | Moisturizer, Moles | Skin Protectant, Moles | Topical Analgesic, Moles | Antiseptic, Moles |
|---|---|---|---|---|---|
| Stearic Acid | 1 (@0.89 wt %) | 1 (@0.889 wt %) | 1 (@2.05 wt %) | 1 (@4.1 wt %) | 1 (@3.75 wt %) |
| DDAC | 1 | 1 | 1 | 0.5 | 0.16 |
| Glycerol Monolaurate[1] | 4 | 4 | 1.5 | 0.59 | 0 |
| Glycerol Monolaurate[2] | 0 | 0 | 0.25 | 0.32 | 0.96 |
| Cetyl Alcohol | 4 | 4 | 1.5 | 1.09 | 0.84 |
| Triethanolamine[1] | 0 | 0.2 | 0.2 | 0.2 | 0.2 |

| Products | Transdermal Device, Moles | Moisturizer, Moles | Skin Protectant, Moles | Topical Analgesic, Moles | Antiseptic, Moles |
|---|---|---|---|---|---|
| DDAS | 1 | 0 | 0 | 0 | 0 |
| Distearyl Stearamide | 0 | 1 | 1 | 0.5 | 0.16 |
| Cetyl Glycerol laurate | 4 | 4 | 1.5 | 0.59 | 0 |

TABLE 4-continued

| | | | | | |
|---|---|---|---|---|---|
| Cetyl Stearate | 0 | 0 | 0 | 0.5 | 0.84 |
| TEA Stearate | 0 | 0 | 0 | 0 | 0 |
| Stearic Acid | 0 | 0 | 0 | 0 | 0 |
| DDAC | 0 | 0 | 0 | 0 | 0 |
| Glycerol Monolaurate | 0 | 0 | 0.25 | 0.32 | 0.96 |
| Cetyl Alcohol | 0 | 0 | 0 | 0 | 0 |

[1] In acid mixture
[2] In neutral mixture

The five compositions decrease in conveyability through the skin surface from complete transmutability in the transdermal composition to total non-absorptivity in the antiseptic composition.

EXAMPLE 14

A composition in accordance with the moisturizer embodiment of Example 13 was prepared. That is, a two-step process was followed in which acidic compounds were first neutralized and then the system was stabilized.

In the first step, the specific components, with their concentration in percentage by weight, based on the total weight of the moisturizer, noted, were provided: distilled water, 13.8%; DDAC, 1.9%; stearic acid, 0.89%; cetyl alcohol, 3.1%; and glycerol monolaurate, 2.35%. These components were heated under continuous stirring at 70° C. for 30 minutes. TEA, 3.45%, was thereupon added at one time and the mass was mixed until a hard solid formed. Ambient temperature distilled water, 4.13%, was then added at ambient temperature and mixed until a smooth mass was obtained.

A separate mass, which comprised the following components, with their concentration indicated, were combined: distilled water, 4.13%, allantoin, 0.4%, aloe vera, 0.25%; and Dimethyl sulfone (MSM), 1%. This mass was heated to 70° C. whereupon the following components were added: propylene glycol, 1.5%; glycerin, 3.5%; lemon oil, 0.4%; vanilla, 0.1%; and olive oil, 20%. This second mixture was cooled to 65° C. and Carbomer 980, 0.5% was added. The mass was mixed until smooth. The two mixtures were combined. Vitamin E, 0.15% and benzethonium chloride, 0.2% were added to the combined mass which was then cooled to ambient temperature. The mixture was mixed under high shear until a smooth and creamy product was obtained, a moisturizing salve containing 20% olive oil.

EXAMPLE 15

Example 14 was repeated but for the addition of TEA in a concentration equal to 0.1 mole % of the stearic acid constituent which was added to the distilled water in the first mass. In accordance with the present invention this addition converts the DDAS, formed in the first step of Example 14, into distearyl stearamide (DSS).

Testing of the Products of Examples 14 and 15

The moisturizer products of Example 14 and 15 were each heated to 170° C. for 30 minutes in a convection oven. They were each allowed to cool in the closed oven for 2 hours. Free oil obtained in each sample was collected and weighed and the concentration of free oil determined. No free oil was obtained from either sample although the sample of Example 15 evidenced visible surface oil.

This test evidences the exceptional stability of both moisturizers albeit establishing a slight superiority of the moisturizer of Example 15.

EXAMPLE 16

Distilled water (1000 g) was mixed with DDAC (19 g), stearic acid (8.9 g), cetyl alcohol (31 g) and glycerol monolaurtate (23.5 g) at 70° C. for 1 hour. Thereupon, TEA (2 g) was added. Gas evolved after 10 minutes at the same 70° C. temperature. The product of this example was replicated but for the replacement of TEA with an equimolar amount of triethanolamine stearate (TEA Stearate). The resultant gas evolution is identical to that noticed when TEA was added.

Analysis of Example 16

This establishes that organic bases such that TEA are equally effective in the salt form as the unprotonated form of to make the amide product from the quaternary compound proceeds to completion.

EXAMPLES 17-24

The following examples, summarized in tabular form in Table 5, illustrate various transdermal compositions. The amounts in Table 5 are weight % of the final product. In the following examples, some of the components have a subscript, such as $TEA_1$, $TEA_2$, etc. The subscript exemplifies the first addition of the component to the mixtures. Thus, $TEA_1$ signifies the first addition of TEA to the mixture, while $TEA_2$ signifies the second addition of TEA to the reaction mixture. The examples also indicates the reaction conditions. The added components and the products are indicated in the following table.

In Table 6, identified products prepared or left unreacted in each example, based on the reaction conditions, such as DDAC, distearyl stearamide, dimethyl distearyl ammonium stearate, cetyl stearate, triethanolamine stearate and the like, are indicated. The products are given as a mole ratio of product relative to stearic acid. Thus, any product present in greater amounts than stearic acid has a mole ratio greater than 1.

TABLE 5

| Composition use Ingredient | Summary of: | | | | | | | |
|---|---|---|---|---|---|---|---|---|
| | Ex. 17 Blister healing | Ex. 18 Bug Bite formula | Ex. 19 Bed Sore Healing | Ex. 20 Minor Cut Formula | Ex. 21 Deep Wound granulation | Ex. 22 Subcutaneous Bruise Healing | Ex. 23 Diaper Rash | Ex. 24 Antiseptic Handwash |
| Acid Reaction Zone | | | | | | | | |
| Water$_1$ | 36.9 | 12.28 | 38.3 | 38.2 | 28.49 | 52.43 | 47.0 | 38.5 |
| Symphytum | .025 | 0 | 0 | 0 | 0 | 0 | 0 | 0 |
| Aloe Vera$_1$ | 0 | 0 | 0 | .08 | .4 | 0 | 0 | 0 |
| TEA$_1$ | .084 | 0 | .084 | 0 | 0 | .039 | .016 | 0.015 |
| DDAC$_1$ | 3.6 | 0 | 3.6 | 3.68 | 3.6 | 1.94 | .44 | .414 |
| Stearic acid | 4.1 | 4.1 | 4.1 | 4.1 | 4.1 | .89 | 3.75 | 3.525 |
| Cetyl alchohol$_1$ | 3.82 | 3.82 | 3.82 | 3.82 | 3.82 | 3.05 | 0 | 0 |
| Glycerol mono-stearate | 3.64 | 0 | 1.96 | 0 | 0 | 3.45 | 0 | 0 |
| Stir @ >70 C. until pH is stable | | | | | | | | |
| TEA$_2$ | .084 | 0 | .084 | 0 | 0 | .039 | .016 | 0.015 |
| Stir@ >70 C. until gas evolution is complete (about 10 minutes) | | | | | | | | |
| TEA$_3$ | 1.55 | .73 | 1.52 | 1.6 | 1.55 | .39 | .09 | .08 |
| Stir@ >70 C. until smooth & creamy | | | | | | | | |
| Water$_2$ | 6 | 30 | 6 | 6 | 6 | 2 | 6 | 6 |
| Aloe Vera$_2$ | .25 | .5 | .1 | .02 | .1 | .25 | 0 | 0 |
| DDAC$_2$ | .9 | 4.5 | 0.9 | .9 | .9 | 0 | .87 | .81 |
| Mix separately until DDAC melts; set aside | | | | | | | | |
| Colostrum | .20 | .2 | .2 | .25 | .75 | 0 | 0 | 0 |
| Arginine | .25 | .25 | .25 | .25 | .4 | 0 | 0 | 0 |
| L-glutamine | .1 | 0 | 0 | 0 | .3 | 0 | 0 | 0 |
| Glycine | .1 | 0 | 0 | 0 | 0 | 0 | 0 | 0 |
| PCA | .1 | .2 | .2 | .2 | .1 | 0 | .1 | .094 |
| Zinc sulfate | .1 | .2 | .2 | .2 | 0 | 0 | 0 | 0 |
| Proline | .1 | .1 | .1 | .1 | .2 | 0 | 0 | 0 |
| Betaine | .1 | 0 | 0 | 0 | 0 | 0 | 0 | 0 |
| Zinc Monomethione | .1 | 0 | 0 | 0 | .3 | 0 | 0 | 0 |
| Bioperine | .08 | .08 | .08 | .08 | .1 | 0 | 0 | 0 |
| Ferulic acid | .08 | .05 | .05 | .05 | .1 | 0 | 0 | 0 |
| Lipoec acid | .08 | .05 | .05 | .05 | .1 | 0 | 0 | 0 |
| Silica gel | .05 | .1 | .1 | .1 | .15 | 0 | 0 | 0 |
| Tetra sodium EDTA | 1.25 | 1.5 | .75 | .75 | .75 | 0 | .3 | .282 |
| MSM$_1$ | .845 | .57 | .192 | .192 | .619 | 1.0 | 0 | 0 |
| Benzethonium chloride | .2 | .2 | .2 | .2 | .2 | .2 | .5 | .5 |
| Dexpanthenol | .63 | .33 | .33 | .33 | .33 | 0 | 0 | 0 |
| Phytantriol | .315 | .11 | .11 | .11 | .11 | 0 | 0 | 0 |
| Tween-80 | .3 | .1 | .1 | 0 | 0 | 0 | 0 | 0 |
| Grape seed extract | .2 | 0 | .1 | .2 | .1 | 0 | 0 | 0 |
| Boswellin | 0 | .15 | .15 | .15 | 0 | 0 | 0 | 0 |
| Berberine HC1 | 0 | .05 | .05 | .05 | 0 | 0 | 0 | .012 |
| Bilberry | 0 | 0 | 0 | 0 | .03 | 0 | 0 | 0 |
| Glucosamine HC1 | 0 | 0 | 0 | 0 | .25 | 0 | 0 | 0 |
| RNA | 0 | 0 | 0 | 0 | .2 | 0 | 0 | 0 |
| Bee Pollen | 0 | 0 | 0 | 0 | .1 | 0 | 0 | 0 |
| OKG | 0 | 0 | 0 | 0 | .1 | 0 | 0 | 0 |
| Cu-Curcumin | 0 | 0 | 0 | 0 | .075 | 0 | 0 | 0 |
| Glycyrrhisic acid | 0 | 0 | 0 | 0 | .05 | 0 | 0 | 0 |
| Honey | 0 | 0 | 0 | 0 | 2 | 0 | 0 | 0 |
| Povidone | 0 | 0 | 0 | 0 | 0 | 0 | .75 | .75 |
| Goldenseal | 0 | 0 | 0 | 0 | 0 | 0 | .15 | 0 |
| Triton-X-100 | 0 | 0 | 0 | 0 | 0 | 0 | 2.5 | 2.35 |

TABLE 5-continued

| | Summary of: | | | | | | | |
|---|---|---|---|---|---|---|---|---|
| Composition use Ingredient | Ex. 17 Blister healing | Ex. 18 Bug Bite formula | Ex. 19 Bed Sore Healing | Ex. 20 Minor Cut Formula | Ex. 21 Deep Wound granulation | Ex. 22 Subcutaneous Bruise Healing | Ex. 23 Diaper Rash | Ex. 24 Antiseptic Handwash |
| Dimethicone | 0 | 0 | 0 | 0 | 0 | 0 | 2.3 | 2.162 |
| Nonoxynol-9 | 0 | 0 | 0 | 0 | 0 | 0 | 2.0 | 1.88 |
| Merquat 550 | 0 | 0 | 0 | 0 | 0 | 0 | 1.15 | 1.081 |
| Crude beeswax | .9 | .9 | .9 | .9 | .6 | 0 | 1.0 | .94 |
| Pregnenolone | .2 | .2 | .2 | .2 | .2 | 0 | 0 | 0 |
| Ascorbyl palmitate | .15 | .15 | .15 | .15 | .2 | 0 | .15 | .141 |
| DHEA | .1 | .1 | .1 | .1 | .1 | 0 | 0 | 0 |
| Shark oil | 1.6 | 2.0 | 2.0 | 2.0 | 1.555 | 0 | 0 | 0 |
| Borage oil-23% | .5 | .432 | .432 | .432 | .42 | 0 | 0 | 0 |
| EPA | .5 | .5 | .5 | .5 | .5 | 0 | 0 | 0 |
| CLA | .5 | .5 | .5 | .5 | .42 | 0 | 0 | 0 |
| Neem oil | .407 | .3 | .3 | .3 | .526 | 0 | 0 | 0 |
| Lemon oil | .2 | .4 | .4 | .4 | .2 | 0 | .5 | 47 |
| Jojoba oil | 0 | 0 | 0 | 0 | .25 | 0 | 0 | 0 |
| Olive oil | 0 | 0 | 0 | 0 | 0 | 5.3 | 0 | 0 |
| Propolis | .3 | .3 | .3 | .3 | .25 | 0 | .4 | .376 |
| Cetyl Alcohol$_2$ | 0 | 0 | 0 | 0 | 0 | 0 | 2.68 | 2.53 |
| Glycerol mono-stearate | 0.4 | 3.7 | 1.74 | 3.7 | 3.6 | 0 | 3.48 | 3.27 |
| Add, in order @ >70 C.; Add DDAC & aloe premix; | Mix until smooth | | | | | | | |
| TEA$_4$ Mix until smooth | 3.78 | 4.17 | 3.27 | 3.30 | 7.65 | 2.26 | 2.84 | 2.04 |
| Propylene glycol | 4.0 | 3.5 | 3.5 | 3.5 | 4.1 | 1.5 | 3.5 | 3.29 |
| Glycerin | .3 | .3 | .3 | .3 | .3 | 3.5 | 0 | 0 |
| Carbomer | .5 | .475 | .5 | .5 | .3 | .75 | .35 | .752 |
| Beta carotene | .016 | .013 | .013 | .013 | .34 | 0 | 0 | 0 |
| Add Process Aids and beta carotene as mix cools to <70 C. | | | | | | | | |
| Water$_3$ | Add quantity sufficient to = 100 | This quantity ≥24% | Add quench water @ temp = 64 C. | | | | | |
| Increase shear rate as mix thickens | | | | | | | | |
| This quench under shear (tip speed >60 in/sec), causes micro crystals to form | | | | | | | | |
| Lidocaine | 2.0 | 2.0 | 1.0 | 1.0 | 2.0 | 0. | 0 | 0 |
| Allantoin | .5 | .15 | .15 | .15 | .4 | .4 | .8 | .5 |
| MSM$_2$ | .155 | .192 | .57 | .57 | .381 | 0 | 0 | 0 |
| Vitamin A | .002 | .002 | .002 | .002 | .06 | 0 | .002 | 0 |
| Vitamin K | .002 | .002 | .002 | .002 | .006 | 0 | .002 | 0 |
| Vitamin D | .002 | .0001 | .001 | .0001 | .006 | 0 | .0001 | 0 |
| Vitamin E | .15 | .15 | .15 | .15 | .25 | .15 | 0 | 0 |
| Lycopene-6% | .1 | 0 | 0 | 0 | 1.104 (12%) | 0 | 0 | 0 |
| Tocotrienol | .08 | .08 | .08 | .08 | .08 | 0 | 0 | 0 |
| Vanilla | .05 | .06 | .06 | .06 | .05 | .1 | 0 | 0 |
| Gotu kola | 0 | 0 | 0 | 0 | .1 | 0 | 0 | 0 |
| Completech | 0 | 0 | 0 | 0 | .1 | 0 | 0 | 0 |
| Forskoli | 0 | 0 | 0 | 0 | .006 | 0 | 0 | 0 |
| Escin | 0 | 0 | 0 | 0 | .006 | 0 | 0 | 0 |
| CHG | 0 | 0 | 0 | 0 | 0 | 0 | 2.55 | 1.275 |
| Vit. E acetate | 0 | 0 | 0 | 0 | 0 | 0 | .25 | .235 |
| Merquard 1200 | 0 | 0 | 0 | 0 | 0 | 0 | .125 | .125 |
| Triclosan | 0 | 0 | 0 | 0 | 0 | 0 | .6 | 0 |
| Povidone iodine | 0 | 0 | 0 | 0 | 0 | 0 | 0 | 6.00 |
| Cool to ambient without mixing | 0 | | | | | | | |

TABLE 5-continued

| | Summary of: | | | | | | | |
|---|---|---|---|---|---|---|---|---|
| Composition use Ingredient | Ex. 17 Blister healing | Ex. 18 Bug Bite formula | Ex. 19 Bed Sore Healing | Ex. 20 Minor Cut Formula | Ex. 21 Deep Wound granulation | Ex. 22 Subcutaneous Bruise Healing | Ex. 23 Diaper Rash | Ex. 24 Antiseptic Handwash |
| Ascorbic acid | 0 | 0 | 0 | 0 | .479 | .096 | 0 | 0 |
| Mineral oil | 0 | 0 | 0 | 0 | 0 | .85 | 0 | 0 |
| Mix @ high shear until creamy & smooth | | | | | | | | |

TABLE 6

PRODUCTS UNDER REACTION CONDITIONS OF EXAMPLES 17-24, EXPRESSED AS MOLE %/MOLE % STEARIC ACID

| Product | Ex. 17 | Ex. 18 | Ex. 19 | Ex. 20 | Ex. 21 | Ex. 22 | Ex. 23 | Ex. 24 |
|---|---|---|---|---|---|---|---|---|
| DDAC | 10.1 | 50.5 | 10.1 | 10.1 | 10.0 | 0 | 9.7 | 9.1 |
| Distearyl stearamide | 40.4 | 0 | 40.4 | 0 | 0 | 21.8 | 4.9 | 4.6 |
| Dimethyl distearyl ammonium stearate | 0 | 0 | 0 | 40.4 | 40.4 | 0 | 0 | |
| Cetyl glycerol laurate | 91 | 0 | 49.5 | 0 | 0 | 87.2 | 0 | 0 |
| Cetyl Stearate | 18.1 | 100.0 | 59.6 | 59.6 | 59.6 | 0 | 0 | 0 |
| Triethanolamine stearate | 41.5 | 0 | 0 | 0 | 0 | 0 | 86.6 | 81.4 |
| Glycerol laurate | 10.1 | 93.5 | 44 | 93.5 | 91 | 0 | 87.9 | 82.6 |
| Cetyl alcohol | 0 | 9.1 | 0 | 49.5 | 49.5 | 0 | 76.7 | 72.3 |

EXAMPLES 25-28

Examples 25-28 teach how to make aromatic and alehatic tertiary amides with saturated and unsaturated fatty acids. In each of Examples 25-28, a quaternary surfactant is added to a fatty acid at a time and temperature sufficient to drive the reaction to completion. As taught above, the conversion to the tertiary amide is a multi-step process. The first step creates a gel; the second step breaks the gel and releases a gas. These two steps iterate back and forth; gel; no gel; gas release; gel; no gel; gas released; and so forth. If the gel is too thick, however, the reaction stops before complete conversion, but the mixture is phase stable and can be transported. Skilled artisans will recognize that more diluent mixture will not visibly gel and more concentrated mixture will visibly gel.

EXAMPLE 25

A 4 quart double boiler was stirred with an Admix, Inc., Londonderry, N.H., RS 29 Optishear 200 Rotosolver™ mixer at 1,000 rpm, 4.5 grams TEA, 1,960 grams distilled water and 112 grams CLA (conjugated linoleic acid) were mixed and heated to about 80° C.

175 grams of benzethonium chloride was added in 7 steps at 44 grams per 15 minutes. After the last benzethonium chloride addition heating was continued at 80° C. for 40 minutes, or until gas release was completed. The net weight of the mixture at the end of Example 25 was 1,812 grams. The released gas smells like methanol. The initial gas release was rapid.

CLA is a floating-on-water fatty acid, liquid at room temperature. Benzethonium chloride is a white powder. The finished product was a milky white, gas-entrained fluid. When analyzed by the USP method for benzethonium chloride, [CPM Laboratory, Inc., Farmers Branch, Tex.; Method CPM 070] the stoichiometric amount of benzethonium chloride was recovered.

The product of Example 25 rubbed into the skin completely in about 15 seconds. It was not sticky; it was an opaque gel. The neat gel has a strong, characteristic-unsaturated-fat odor. After rubbing Example 25 gel into the skin, there is only a faint residual odor on the skin. It is theorized that the unsaturated bonds have penetrated the SC while the aromatic branches have not penetrated the SC.

The Example 25 product is benzethonium linoleamide (BLA).

EXAMPLE 26

Using the apparatus in Example 25, 1,200 grams distilled water, 57 grams CLA, and 5.5 grams TEA were mixed together and the mixture was heated to 80° C. 120 grams dimethyl distearyl ammonium chloride was added at a rate of 20 grams/10 minutes. After the last dimethyl distearyl ammonium chloride addition, heating was continued at 80C for 10 minutes or until the gas release was complete. The gas release in Experiment 26 was slow. "Pinprick" bubbles would be seen percolating to the top of the reaction fluid. The weight of the mixture at the end of Example 26 was 991 grams.

The cooled product of Example 26 was a white precipitate. The Example 26 precipitate rubs into the skin in about 20 seconds. There is no residual odor on the skin. The skin has an obvious coating on it with a perceived coefficient of friction greater than the untreated skin.

The Example 26 product is distearyl linoleamide (DSL).

EXAMPLE 27

Using the Example 25 apparatus, 1,200 grams distilled water, 53 grams stearic acid and 1.1 grams TEA were heated to 80° C. 84 grams of benzethonium chloride was added, stepwise at a rate of 14 grams/10 minutes. After the last benzethonium chloride addition, heating was continued at 80° C. for 20 minutes or until the gas release was complete (the fluid remains full of gas, but gas is not released from the surface). The weight of the mixture at the end of Example 27 was 929 grams.

The cooled product of Example 27 was a white, gaseous fluid. The Example 27 product rubs into the skin in about 15 seconds. There is no odor and the product is not perceived on the skin.

The Example 27 product is benzethonium stearamide (BSA).

EXAMPLE 28

Using the Example 25 apparatus, 1,200 grams distilled water, 53 grams stearic acid and 5.5 grams TEA was heated to 80° C. 115 grams dimethyl distearyl ammonium chloride was added, stepwise, at 19 grams/10 minutes. Heating was continued at 80C for 10 minutes or until the gas release was complete. The weight of the mixture at the end of Example 28 was 988 grams.

The cooled product of Example 28 was a greasy white solid. The Example 28 product rubs into the skin in about 20 seconds. There was no odor. The skin has a readily perceived dry coating after rub-in.

The Example 28 product was distearyl stearamide (DSS).

EXAMPLE 29

Example 29 illustrates intentionally incomplete conversion with unsaturated fatty acids.

Using the Example 25 apparatus, except the stirring rate was 2,000 rpm, 960 grams distilled water, 1.2 grams TEA, 112 grams CLA was heated to 80° C. 32 grams benzethonium chloride was added thereto. Agitated heating was continued at 80C for 25 minutes. 63 grams borage oil was added thereto. Borage oil is an unsaturated fatty acid with about 23% $C_{18:3}$; the rest of borage oil is largely $C_{18:2}$. 8 grams of additional TEA and 323 grams dimethyl distearyl ammonium chloride were added. The agitated heating was continued for an additional 50 minutes at 80C.

The Example 29 mixture was allowed to cool to ambient temperature. The final weight was 1,094 g. Example 29 is sufficiently phase stable to be added at a later time to Example 30 without additional mixing. The conversion of the quaternary surfactants and fatty acids to tertiary amides are intentionally incomplete such that a meta stable grease is formed that can be stored and transported for later use as a premix.

Example 29 contains BLA and DSL.

EXAMPLE 30

In Example 30, the Example 29 unsaturated premix was diluted with water to allow the no gel step to occur and the reaction to go to completion. The product was made into a finished product.

Example 30 is a wound care product designed to induce granulation in chronic wounds that require skin granulation to heal completely.

9,365 grams of distilled water was heated with 656 grams stearic acid and 243 grams of dimethyl distearyl ammonium chloride to 70C for 15 minutes in a 5 gallon round bottom mixing kettle with an Admix Rotosolver agitator (2.84 inch diameter) at 300 rpm. 611 grams cetyl alcohol was added to the water mixture and heated for 35 minutes at 70-80° C. 120 g EDTA, 120 g colostrum, 108 g MSM, 64 g arginine, 48 g L-glutamine, 48 g bilberry, 48 g L-opti zinc, 40 g glucosamine, 32 g proline, 32 g RNA, 24 g silica gel, 16 g bee pollen, 16 g ornithine ketoglutarate (hereinafter "OKG"), 16 g bioperine, 16 g ferulic acid, 16glipoec acid, 12 g Cu-curcumin, 8 g glycrrhizic acid, 53 g dexpanthenol, 32 g honey, 18 g phytantriol, 256 g shark oil, 64 g neem oil, 64 g eicosapentaenoic acid (hereinafter "EPA"), 40 g jojoba oil and 32 g lemon oil were added and heated at 70-80C for 5 minutes at a mixing rate of 350 rpm.

51 g TEA was added. The mixture was heated for 5 minutes at 70-80° C. 143 g of dimethyl distearyl ammonium chloride, 80 g aloe vera, 16 g grape seed extract and 1,413 g TEA were added. The mixture was heated for 5 minutes at 70-80° C.

576 g Lauricidin, 96 g beeswax, 32 g pregnenolone, 32 g ascorbyl palmitate and 16 g DHEA were added thereto and the ingredients were mixed together for 5 minutes at 70-80° C. The Example 29 premix (1,094 g) was added. The agitator speed was increased to 450 rpm. The mixture was allowed to cool. Then 4 g of propolis was added at 71° C. 640 g propylene glycol and 48 g glycerin at 70° C. was added thereto. 48 g Carbomer 980 NF at 68° C. was added. At 65° C., 54 g 95% beta carotene was added and agitation was increased to 600 rpm.

At 62° C., agitation was increased to 1,000 rpm. At 56C, agitation was increased to 1,300 rpm. At 55° C., 320 g lidocaine was added, 64 g allantoin, 52 g MSM, 16 g Gotu Kola, 1 g of escin, 1 g of forskoli, 1 g each of Vitamins A, D, K, 320 g 6% lycopene, 40 g Vitamin E and 13 g tocotrienol were added to the mixture and the contents were mixed for 2 minutes.

It was cooled to ambient temperature, and 82 g rams ascorbic acid was added at an agitation speed of 2,850 rpm and mixed for 3 minutes.

Example 30 product was applied to chronic, deep, diabetic foot ulcers that had not healed in 1-3 years. All treated ulcers were completely healed within 60-90 days after treatment.

EXAMPLE 31

The example illustrates an intentionally incomplete conversion with saturated fatty acids.

In a 5 gallon round-bottomed cooking kettle with a centered, Admix Rotosolver agitator (2.84" diameter), 12,525 g distilled water was heated with 88 g TEA, 1,673 g stearic acid and 1,320 g benzethonium chloride to 80C at 350 rpm for 20 minutes.

1,817 g dimethyl distearyl ammonium chloride was added thereto and the mixture was heated 10 additional minutes at 80° C. The net weight was 17,000 g.

Example 31 is an intentionally incomplete reaction. Example 31 is a meta-phase stable semi-solid premix that can be stored, transported and used without remixing.

EXAMPLE 32

In Example 32, the Example 31 saturated premix is diluted with water to complete the reaction and then made into a more neutral pH finished product.

In a 20 gallon round-bottomed kettle with an off-center Admix Rotosolver agitator (2.84" diameter), 29,554 g distilled water was heated with 2,132 g stearic acid and 3,950 g of the Example 31 product to 80° C. for 10 minutes at 600 rpm. The mix released a large amount of gas as the Example 31 reactions go to completion in the diluted, visibly-gel-free environment of Example 32.

1,771 g of cetyl alcohol was added and heated at 70-80° C. for 50 minutes. Cetyl stearate was formed in this step.

495 g povidone, 198 g EDTA, 66 g PCA, 10 g goldenseal, 70 g TEA and 569 g dimethyl distearyl ammonium chloride were added and mixed at 750 rpm for 5 minutes at 70-80° C.

1,863 g TEA, 2,293 g Lauricidin, 660 g beeswax, 99 g ascorbyl palmitate, 1,650 g Triton X-100, 1,518 g dimethicone, 1,320 g nonoxynol-9, 759 g Merquat 550 and 330 g lemon oil were added. The speed was increased to 1,300 rpm and mixed 5 minutes at 70-80° C. The heat was turned off.

265 g propolis at 71° C. was added. The mixture was 2,310 g propylene glycol was added at 70° C. 265 g Carbomer 940NF was next added at 68° C.

At 65 C, agitation was increased to 1,600 rpm. At 60C, agitation was increased to 2,000 rpm and 11,418 g distilled water was added thereto.

At 55° C. or less, the speed was increased to 3,000 rpm. 165 g Vitamin E acetate, 83 g Merguard 1200, 264 g allantoin, L3 g Vitamin A, 0.07 g Vitamin D, 396 g triclosan and 4,422 g chlorhexidine gluconate (CHG) solution was added and mixed 2 minutes.

Cool to ambient in 5 gallon covered pails. Each pail was mixed for 3 minutes at 2,850 rpm. The yield is 66,000 g.

Example 32 product is an anti-bacterial skin protectant. It is non-irritating, non sticky and moisturizes the skin. It provides persistent antibacterial protection for up to 6 hours. The pH of Example 32 increases as it cools. The ambient pH is 7.3. Example 32 product is stable for 2 years.

EXAMPLE 33

In this example the Example 31 saturated premix was made into an acid ph finished product.

Example 33 is a persistent antiseptic skin protectant made with the Example 31 premix. Example 33 contains povidone iodine. Povidone iodine is normally not stable at pH>4.5.

In the apparatus of Example 32, 30,272 g distilled water was mixed with 2,057 g stearic acid and 4,249 g of Example 31 saturated premix for 10 minutes at 70-80C at 350 rpm. Gas was released as the Example 31 reactions went to completion. 1,771 g cetyl alcohol was added thereto and the mixture was heated for 50 minutes at 70-80° C.

495 g povidone, 198 g EDTA, 66 g PCA, 110 g TEA and 404 g dimethyl distearyl ammonium chloride were added and the mixing speed was increased to 750 rpm. The mixture was heated 5 minutes at 70-80C.

534 g TEA, 2,496 g Lauricidin, 660 g beeswax, 1,518 g dimethicone, 1,650 g Triton X-100, 1,320 Nonoxynol-9 and 792 g Merquat 550 were added to the mixture. The mixing speed was increased to 1,300 rpm. Then the mixture was heated at 70-80° C. for 5 minutes. The heat was turned off and the mixture began cooling.

264 g propolis was added at 71C.

2,310 g propylene glycol was added at 70C, 581 g Carbomer 940 NF was added at 68C. At 65° C., the mixing speed was increased to 1,600 rpm.

At 60° C., the mixing speed was increased to 2,000 rpm and 11,418 g distilled water was added. 99 g Merquard 1200 and 825 g CHG solution were added.

The mixture was cooled in 5 gallon pails. At ambient temperature, the mixture was whipped 3 minutes at 3,300 rpm. About one day after whipping, 4,950 g povidone iodine was added, mixing at 2,850 rpm for one minute.

The final pH is 4.4. The iodine was stable for at least one year.

Example 33 product not only reduced the microbial counts on the hands one minute after application, it also reduced the counts 6 hours after application, making Example 33 a persistent antiseptic.

The FDA temporary final monograph for Health-Care Antiseptic Drug Products defines an antiseptic hand wash as "an antiseptic containing preparation designed for frequent use; it reduces the number of transient microorganisms on intact skin to an initial base line level after adequate washing rinsing and drying, It is broad spectrum, fact acting and possible, persistent". The FDA definition underscores the difficulty of making an antiseptic persistent.

EXAMPLE 34

In Example 34 a moisturizing production made with a water extract of Lilium Longiflorum lily root extract. Example 34 illustrates how cetyl glycerol laurate (CGL) and distearyl stearamide (DSS) are made in situ. The Example 34 product is useful for treating various types of skin cancer.

In the apparatus of Example 32, 20,611 g distilled water were mixed with 17.6 g TEA, 874 g dimethyl distearyl ammonium chloride and 402 g stearic acid. The stirring rate was 1,000 rpm. The mixture was heated to 70-80C for 10 minutes. [The conversion to DSS begins, but does not go to completion.] 1,374 g cetyl alcohol and 1,553 g Lauricidin (glycerol monolaurate) were added. The mixture was heated 50 minutes at 70-80C. [The cetyl alcohol converts to cetyl stearate, then to cetyl glycerol laurate (CGL) and stearic acid. The stearic acid eventually is converted to DSS.]

An additional 17.6 g TEA was added, to the mixture. The mixture was heated for 10 minutes at 70-80° C. 194 g TEA was added and the mixture heated for 5 minutes at 70-80° C. at 1,300 rpm. 2,385 g olive oil and 90 g benzethonium chloride and 833 g TEA were added to the mixture. The heat was turned off and the reaction mixture was allowed to cool.

675 g propylene glycol and 1,575 g glycerin were added to the mixture at 70° C. The stirring speed was increased to 1,600 rpm at 68° C.; 293 g Carbomer 940NF was added to the mixture. At 67° C., stirring was increased to 2,000 rpm.

At 66C, stirring was increased to 2,500 rpm; 14,850 g of lily root extract was next added to the mixture.

The mixture was cooled to ambient in 5 gallon pails. The mixture was stirred at 3,300 rpm; add 383 g mineral oil and 90 g vanilla extract.

Example 34 is a moisturizing lotion with an unexpected skin care benefit. Users with skin cancer were cured. Various other herbal extracts can be substituted for the lily root extract.

EXAMPLE 35

In Example 35, a moisturizing product made with a water extract of Lilium Longiflorum is made using the premix of Example 31 and a beeswax occlusive layer instead of the mineral oil occlusive layer used in 34. The Example 31 premix includes BSA and DSS.

In the apparatus of Example 32, 26,117 g of distilled water is mixed with 3,960 g of Example 31 premix, 172 g stearic acid, 600 g dimethyl distearyl ammonium chloride, 2,047 g cetyl alcohol and 4,293 g Lauricidin. The stirring rate was 600 rpm. The mix is heated to 80° C. for 60 minutes. [The premix reactions of to completion and the cetyl alcohol and Lauricidin convert to cetyl glycerol laurate.] 703 g TEA was added and mixed for 5 minutes at 80° C.

66 g PCA, 660 g MSM and 495 g povidone are added to the mix and stirred for 5 minutes at 80° C.

1,079 g TEA are added to the mix and stirred at 80° C. at 1,000 rpm for 5 minutes.

165 g aloe vera, 660 g beeswax, 264 g lemon oil and 3,300 g olive oil are added to the mix and stirred for 5 minutes at 80° C.

990 g propylene glycol are added at 70° C. 363 g Carbomer 980NF are added at 68° C.

At 64°, the stirring rate is increased to 1,300 rpm. 21,780 g of ambient water extract of lily root is added substantially all at once. The temperature drops down to less than 55° C. and microspheres are formed.

The stirring rate is increased to 1,600 rpm. 462 g allantoin, 198 g palm tocotrienol, 1.3 g each of Vitamins A, D and K are added to the mix.

The mix is cooled to ambient temperature in 5 gallon pails, then each pail is stirred at 2,850 rpm for 3 minutes. 63 g of ascorbic acid are added proportionately to each pail during whipping.

Example 35 is a moisturizing skin protectant with a soft silky feel as opposed to the greasy feel that comes from using mineral oil.

EXAMPLE 36

Example 36 shows how to make cetyl glycerol laurate (CGL).

1,200 g distilled water, 5 g benzethonium chloride, 6 g stearic acid are mixed together in the Example 25 apparatus and stirred at 1,000 rpm and heated to 80° C.

100 g cetyl alcohol and 113 g Lauricidin are added to the mix and heated for 75 minutes at 80° C.

5 g benzethonium chloride is added and cooked at 80° C. for 10 minutes.

The Example 36 mixture was allowed to cool to ambient temperature. The final weight was 1,053 g.

The Example 36 mixture rubs into the skin in about 10 seconds. It is a white grease.

The initial benzethonium chloride and stearic acid lower the pH. There is a small molar excess of stearic acid. The cetyl alcohol reacts with the excess stearic acid and then with the Lauricidin. After 75 minutes, substantially all the cetyl alcohol and all the Lauricidin are reacted.

Benzethonium chloride is added to react with the excess stearic acid.

Example 36 contains a small amount of BSA and a substantial amount of CGL in water.

EXAMPLE 37

The composition of Example 20 was replicated except that the benzethonium chloride was added at a temperature lower than the freezing point of stearic acid, i.e., at 55° C.

There was an immediate unexpected increase in the level of mixing vessel and a temperature drop greater than the temperature drop associated with the sensible heat of adding ambient temperature ingredients.

Analysis of Example 37

Benzethonium chloride reacted with the still-liquid unsaturated fatty acids in the mix to form the tertiary amide and methanol gas. Benzethonium chloride did not react with the stearic acid because the temperature was below the melting point of stearic acid. Benzethonium chloride did not react with stearic acid in Example 20 because of the presence of inhibitors such as aloe Vera.

The gas entrained in the mix accounts for the increased level. The endothermic temperature drop is seen when tertiary amides form.

The above preferred embodiments and examples are given to illustrate the scope and spirit of the present invention. These embodiments and examples will make apparent to those skilled in the art other embodiments and example. These other embodiments are within the contemplation of the present invention. Therefore, the present invention should be limited only by the appended claims.

What is claimed is:

1. A compound having the formula

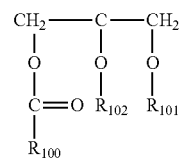

wherein $R_{100}$ is fatty groups having 11-29 carbon atoms and $R_{101}$ and $R_{102}$ are independently a fatty group having 12-30 carbon atoms.

2. The compound according to claim 1 wherein $R_{100}$, $R_{102}$, and $R_{101}$ independently contain 16-22 carbon atoms.

3. A carrier composition comprising the compound of claim 1.

4. A carrier composition comprising the compound of claim 2.

5. A method for enhancing the penetration of a drug through the skin of a mammal which comprises mixing the drug with a skin penetrating effective amount of the compound of the formula

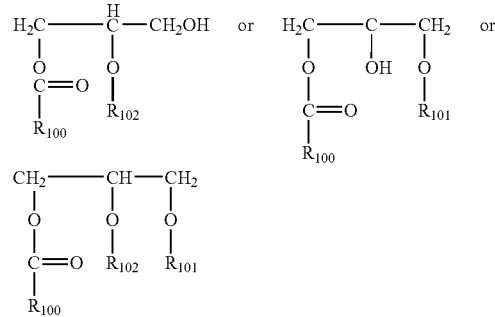

wherein $R_{100}$ is fatty groups having 11-29 carbon atoms and $R_{101}$ and $R_{102}$ are independently a fatty group having 12-30 carbon atoms.

6. A compound having the formula selected from the group consisting of

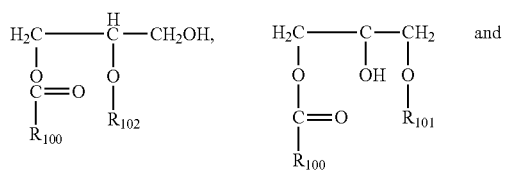

-continued

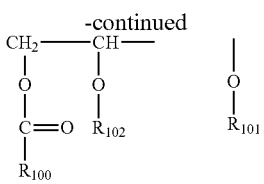

wherein $R_{100}$ is fatty groups having 11-29 carbon atoms and $R_{101}$ and $R_{102}$ are independently a fatty group having 12-30 carbon atoms admixed with a quaternary ammonium salt of the formula

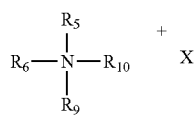

wherein $R_5$, $R_6$, $R_9$ and $R_{10}$ are independently lower alkyl, fatty group, aryl lower alkyl or $R_7$ wherein at least one of $R_5$, $R_6$, $R_9$ and $R_{10}$ is a fatty group, each of said fatty group containing 11-29 carbon atoms and may be completely saturated or contain 1-8 carbon-carbon double bonds, $R_7$ is

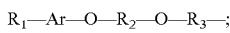

$R_1$ is alkyl containing 1-15 carbon atoms,
$R_2$ and $R_3$ are independently lower alkylene, and
X is a counter ion.

7. A carrier composition comprising a compound having the formula selected from the group consisting of

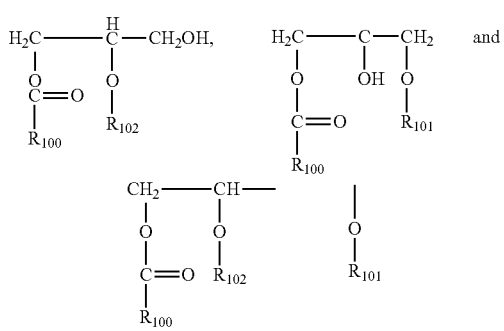

wherein $R_{100}$ is fatty groups having 11-29 carbon atoms and $R_{101}$ and $R_{102}$ are independently a fatty group having 12-30 carbon atoms admixed with a quaternary ammonium salt of the formula

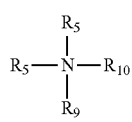

wherein $R_5$, $R_6$, $R_9$ and $R_{10}$ are independently lower alkyl, fatty group, aryl lower alkyl or $R_7$ wherein at least one of $R_5$, $R_6$, $R_9$ and $R_{10}$ is a fatty group, each of said fatty group containing 11-29 carbon atoms and may be completely saturated or contain 1-8 carbon-carbon double bonds, $R_7$ is

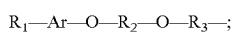

$R_1$ is alkyl containing 1-15 carbon atoms,
$R_2$ and $R_3$ are independently lower alkylene, and
X is a counter ion.

8. A pharmaceutical composition for topical application comprising a pharmaceutically effective amount of a drug and the carrier composition of claim 7.

9. The pharmaceutical composition according to claim 7 wherein the drug and the carrier are present in a molar ratio of drug to carrier of greater than about 20.

10. The pharmaceutical composition according to claim 8 wherein the drug and the carrier are present in a molar ratio of between about 5 and about 20.

11. A method for treating skin sores, chapping, chafing, skin bruises or wounds on a mammal which comprises applying to the locus of the skin injury a pharmaceutical composition comprising a pharmaceutically effective amount of a drug and a skin penetrating effective amount of a carrier composition comprised of a compound having the formula selected from the group consisting of

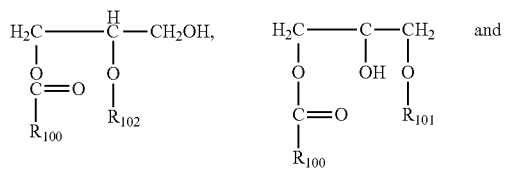

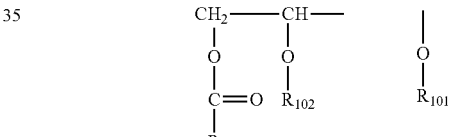

wherein $R_{100}$ is fatty groups having 11-29 carbon atoms and $R_{101}$ and $R_{102}$ are independently a fatty group having 12-30 carbon atoms.

12. The pharmaceutical composition according to claim 11 wherein the drug and the carrier are present in a molar ratio of drug to carrier ranging from between about 5 to about 20.

13. A composition comprising a compound having the formula selected from the group consisting of

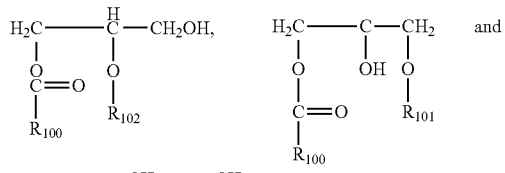

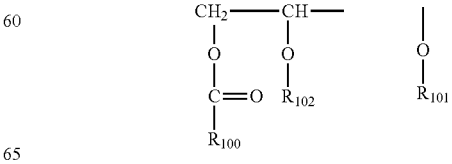

wherein $R_{100}$ is fatty groups having 11-29 carbon atoms and $R_{101}$ and $R_{102}$ are independently a fatty group having 12-30 carbon atoms and a tertiary amide of the formula

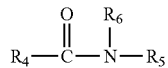

or pharmaceutically acceptable salts thereof,
wherein $R_4$ is a fatty group of 11-29 carbon atoms;
$R_5$ and $R_6$ are independently lower alkyl, aryl, aryl lower alkyl, or fatty group containing 11-29 carbon atoms or $R_7$;
$R_7$ is

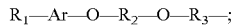

$R_2$ and $R_3$ are independently lower alkylene groups containing 1-6 carbon atoms,
$R_1$ is a lower alkyl, and
Ar is aryl.

14. The composition according to claim 13 additionally comprising nutrients and antioxidants.

15. The composition according to claim 13 wherein $R_4$ is a fatty group containing 15-21 carbon atoms.

16. The composition according to claim 15 wherein $R_5$ is aryl or aryl lower alkyl; and $R_6$ is

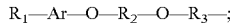

$R_2$ and $R_3$ are independently alkylene containing 1-3 carbon atoms; and
Ar is aryl.

17. The composition according to claim 16 wherein Ar is phenyl.

18. The composition according to claim 17 wherein $R_5$ is aryl lower alkyl.

19. The composition according to claim 18 wherein $R_5$ is benzyl.

20. The composition according to claim 18 wherein $R_4$ is saturated.

21. The composition according to claim 19 wherein $R_4$ is unsaturated.

22. The composition according to claim 21 wherein $R_4$ contains 1-8 carbon-carbon double bonds.

23. The composition according to claim 13 wherein the tertiary amide is distearyl stearamide, distearyl linoleamide,

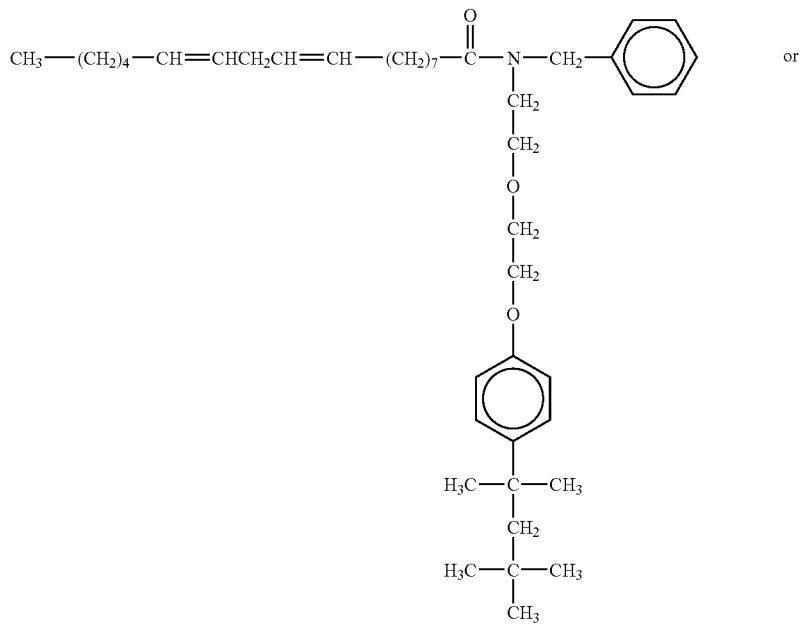

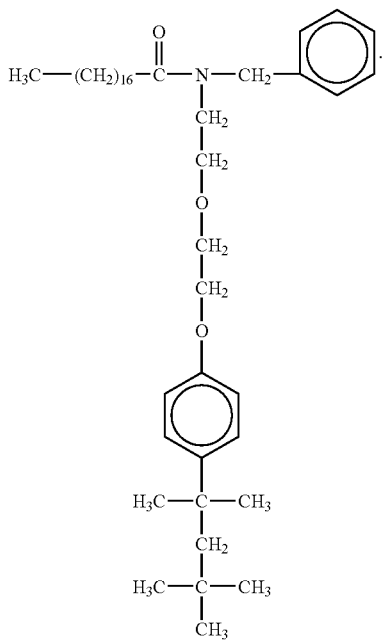

24. A composition comprising a compound having the formula selected from the group consisting of

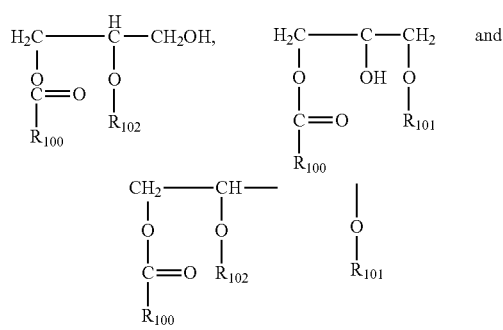

wherein $R_{100}$ is fatty groups having 11-29 carbon atoms and $R_{101}$ and $R_{102}$ are independently a fatty group having 12-30 carbon atoms and a tertiary amide hydrate, wherein, the tertiay amide has the formula

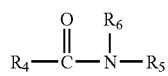

or pharmaceutically acceptable salts thereof wherein $R_4$ is a fatty group of 11-29 carbon atoms;

$R_5$ and $R_6$ are independently lower alkyl, aryl, aryl lower alkyl, or fatty group containing 11-29 carbon atoms or $R_7$;

$R_7$ is $R_1$—Ar—O—$R_2$—O—$R_3$—;

$R_2$ and $R_3$ are independently alkylene groups containing 1-6 carbon atoms;

$R_1$ is an alkyl group containing 1-15 carbon atoms; and

Ar is aryl;

said fatty group being either completely saturated or containing 1-8 carbon-carbon double bonds.

25. The composition of claims 24 wherein $R_4$ is a fatty group containing 15-21 carbon atoms.

26. The composition of claim 24 wherein $R_5$ is aryl or aryl lower alkyl; and $R_6$ is $R_1$—Ar—O—$R_2$—O—$R_3$—;

$R_2$ and $R_3$ are independently alkylene containing 1-3 carbon atoms; and

Ar is aryl.

27. The composition of claim 26 wherein Ar is phenyl.

28. The composition of claim 27 wherein $R_5$ is aryl lower alkyl.

29. The composition according to claim 28 wherein $R_5$ is benzyl.

30. The composition according to claim 28 wherein $R_4$ is saturated.

31. The composition according to claim 28 wherein $R_4$ is unsaturated.

32. The composition according to claim 28 wherein $R_4$ contains 1-8 carbon-carbon double bonds.

33. The composition according to claim 24 wherein the tertiary amide of the tertiary amide hydrate is selected from the group consisting of distearyl stearamide, distearyl linoleamide,

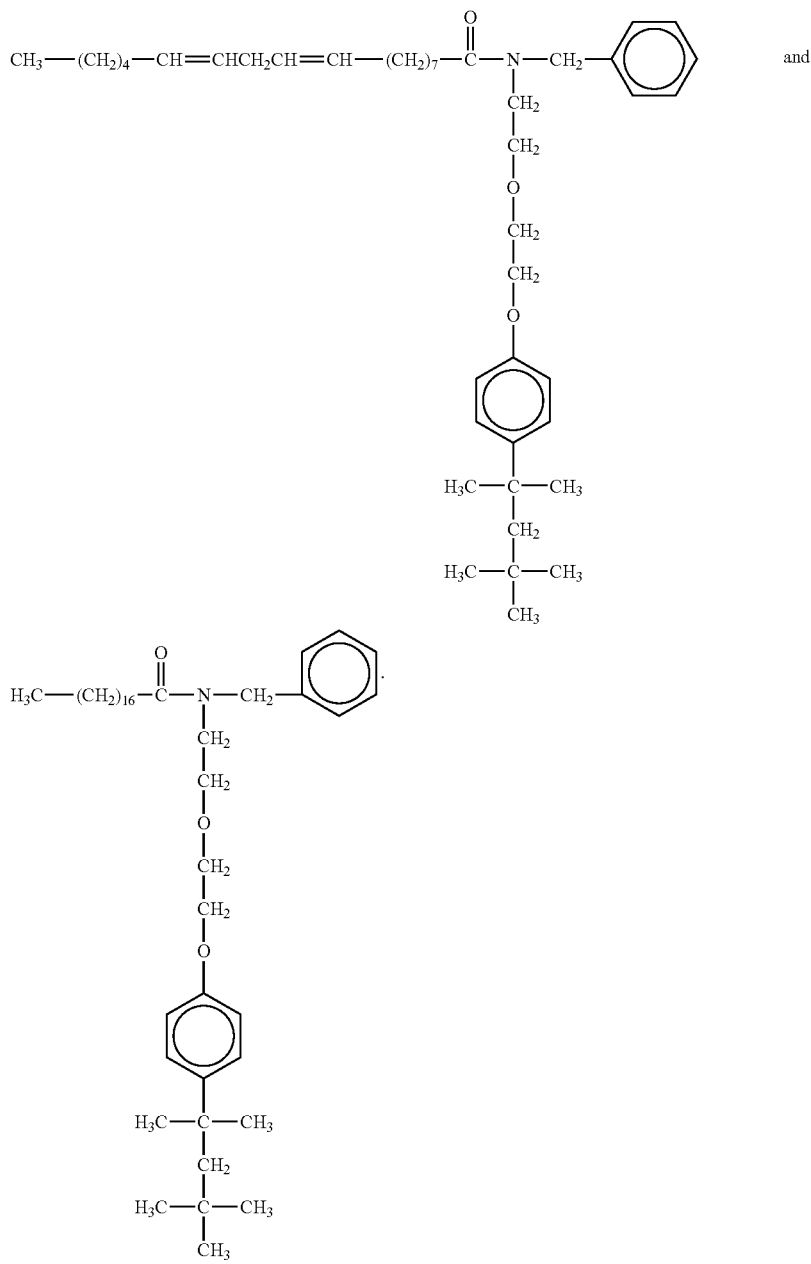

and

34. The composition according to claim 13 wherein the compound has the formula

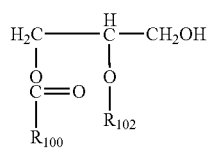

wherein $R_{100}$ is fatty group containing 13 carbon atoms and $R_{102}$ is fatty group containing 16 carbon atoms.

35. The composition according to claim 24 wherein the compound has the formula

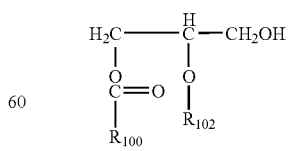

wherein $R_{100}$ is fatty group containing 13 carbon atoms and $R_{102}$ is an alkyl group containing 16 carbon atoms.

36. The composition according to claim 13 wherein the compound has the formula

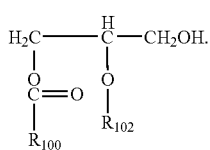

37. The composition according to claim 24 wherein the compound has the formula

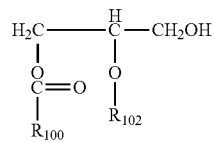

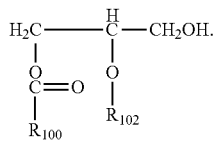

38. A compound having the formula

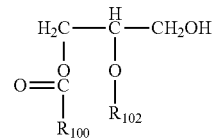

wherein $R_{100}$ is a fatty group having 11, 12, 14, 15, 16, 17 and 19-29 atoms and $R_{102}$ contains 12-15, 17, 19-30 atoms.

39. A carrier composition compound of claim 38.

40. A compound having the formula

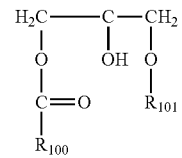

wherein $R_{100}$ is a fatty group having 11-15 and 17-29 carbon atoms and $R_{101}$ is a fatty group having 12-15 and 17-30 carbon atoms.

41. A carrier composition comprising the compound of claim 40.

* * * * *